(12) United States Patent
Delis et al.

(10) Patent No.: US 10,657,837 B2
(45) Date of Patent: *May 19, 2020

(54) MULTI-LEVEL EXECUTIVE FUNCTIONING TASKS

(71) Applicant: Pearson Education, Inc., New York, NY (US)

(72) Inventors: Dean Delis, Encinitas, CA (US); James Holdnack, Bear, DE (US); Lisa Drozdick, San Antonio, TX (US)

(73) Assignee: PEARSON EDUCATION, INC., New York, NY (US)

( * ) Notice: Subject to any disclaimer, the term of this patent is extended or adjusted under 35 U.S.C. 154(b) by 49 days.

This patent is subject to a terminal disclaimer.

(21) Appl. No.: 15/858,139

(22) Filed: Dec. 29, 2017

(65) Prior Publication Data

US 2018/0336791 A1 Nov. 22, 2018

Related U.S. Application Data

(63) Continuation-in-part of application No. 15/599,050, filed on May 18, 2017.

(51) Int. Cl.
| | |
|---|---|
| G09B 7/04 | (2006.01) |
| G09B 19/00 | (2006.01) |
| G09B 5/06 | (2006.01) |
| A61B 5/00 | (2006.01) |
| G06F 3/0488 | (2013.01) |
| G06F 3/0482 | (2013.01) |

(52) U.S. Cl.
CPC .............. *G09B 7/04* (2013.01); *A61B 5/0022* (2013.01); *A61B 5/4088* (2013.01); *A61B 5/7435* (2013.01); *A61B 5/7475* (2013.01); *G09B 5/065* (2013.01); *G09B 19/00* (2013.01); *G06F 3/0482* (2013.01); *G06F 3/04883* (2013.01)

(58) Field of Classification Search
CPC . A61B 5/0022; A61B 5/04842; A61B 5/4064; A61B 5/162; A61B 5/4088; A61B 5/7475; G09B 7/02; G09B 19/00; G09B 7/04; G09B 5/00; G09B 5/02; G09B 5/06; G09B 5/065; G09B 7/00
See application file for complete search history.

(56) References Cited

U.S. PATENT DOCUMENTS

2007/0141541 A1 6/2007 Chan et al.
2010/0055659 A1 3/2010 Rogers et al.
(Continued)

OTHER PUBLICATIONS

Findlay J. et al. "Saccade target selection: Do distractors affect saccade accuracy?" Vision Research 49 (2009) pp. 1267-1274.

*Primary Examiner* — Jerry-Daryl Fletcher
(74) *Attorney, Agent, or Firm* — Quarles and Brady LLP

(57) ABSTRACT

Systems and methods of the present invention provide for generating a first, second, and third series of interface objects comprising a first and second sequence respectively, displayed on a graphical user interface (GUI). At least one visual indicator display object is also displayed that requires a switch between the first and second series of user interface objects. A user navigates through the first and second series of interface objects, including the visual indicator display object(s), and a score for the user is calculated according to a user input matching, or failing to match, a correct response associated with a task data defining a function skill demonstrating a cognitive ability of the user.

18 Claims, 19 Drawing Sheets

(56) References Cited

U.S. PATENT DOCUMENTS

2014/0163426 A1  6/2014  Alberts et al.
2014/0370479 A1  12/2014  Gazzaley
2017/0112427 A1  4/2017  Simon et al.

MULTI-LEVEL EXECUTIVE FUNCTIONING TASKS

CROSS REFERENCE TO RELATED PATENT APPLICATIONS

This patent application is a continuation-in-part of, and claims priority to, U.S. patent application Ser. No. 15/599,050 filed May 18, 2017 and titled "MULTI-LEVEL EXECUTIVE FUNCTIONING TASKS."

FIELD OF THE INVENTION

This disclosure relates to the field of systems and methods configured to administer executive functioning tests, sub-tests, and tasks and analyzing input from a client machine in order to detect a cognitive decline, possibly caused by neurological or psychiatric insult, and possibly detecting early stage disease, and specifically to execute software logic within the systems in order to administer the tests, subtests, and tasks in order to generate results and evaluate examinees via the disclosed system.

SUMMARY OF THE INVENTION

The present invention provides systems and methods comprising one or more server hardware computing devices or client hardware computing devices, communicatively coupled to a network, and each comprising at least one processor executing specific computer-executable instructions within a memory that, when executed, cause the system to: generate a first, second, and third series of interface objects comprising a first and second sequence respectively, displayed on a graphical user interface (GUI). At least one visual indicator display object is also displayed that requires a switch between the first and second series of user interface objects. A user navigates through the first and second series of interface objects, including the visual indicator display object(s), and a score for the user is calculated according to a user input matching, or failing to match, a correct response associated with a task data defining a function skill demonstrating a cognitive ability of the user.

The above features and advantages of the present invention will be better understood from the following detailed description taken in conjunction with the accompanying drawings.

DETAILED DESCRIPTION

Figure 1:
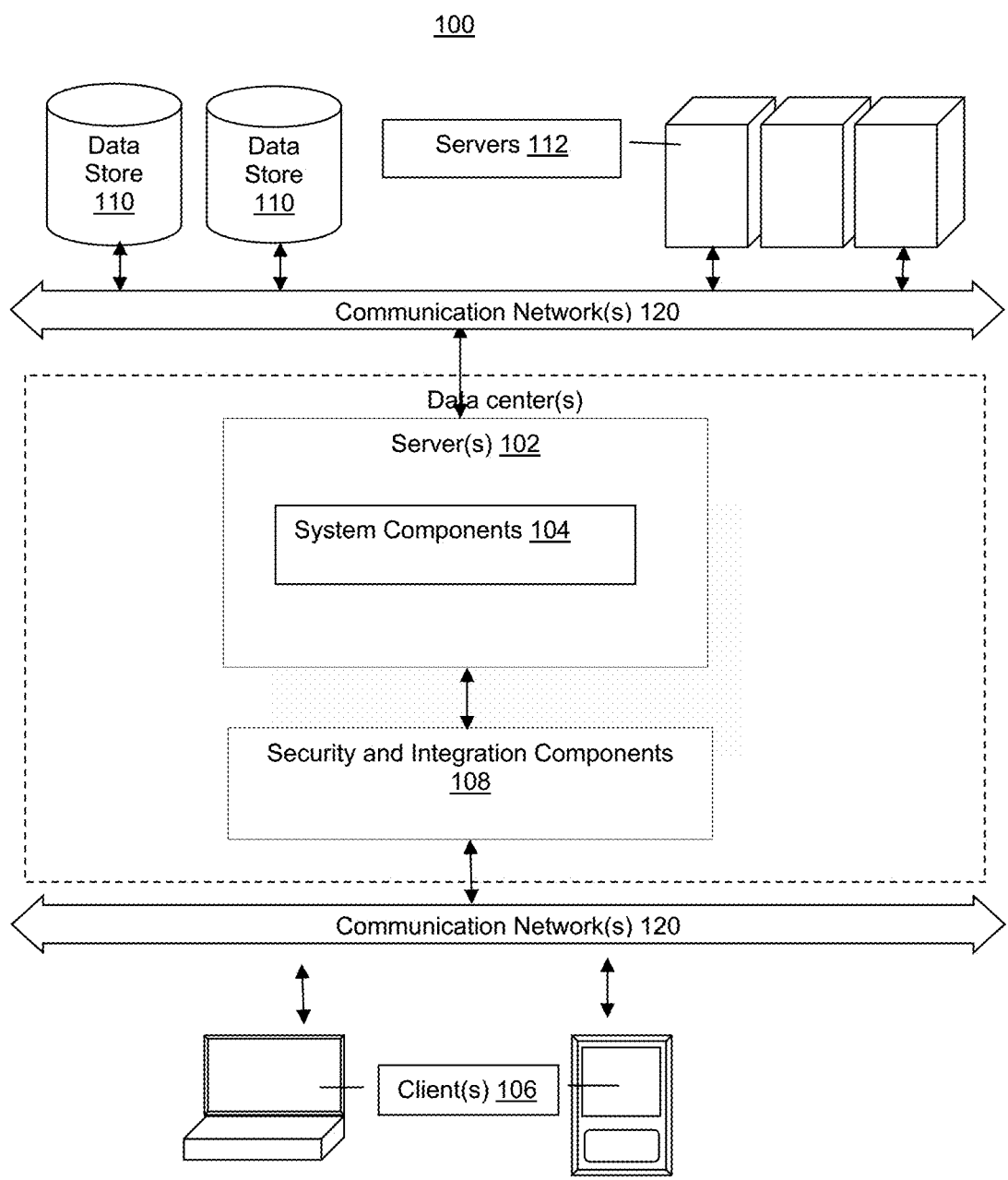
FIG. 1 illustrates a system level block diagram for administering and scoring multiple level executive functioning tests and tasks.

The present inventions will now be discussed in detail with regard to the attached drawing figures that were briefly described above. In the following description, numerous specific details are set forth illustrating the Applicant's best mode for practicing the invention and enabling one of ordinary skill in the art to make and use the invention. It will be obvious, however, to one skilled in the art that the present invention may be practiced without many of these specific details. In other instances, well-known machines, structures, and method steps have not been described in particular detail in order to avoid unnecessarily obscuring the present invention. Unless otherwise indicated, like parts and method steps are referred to with like reference numerals.

Declines in higher-level cognitive skills, commonly referred to as executive functions, are frequently one of the earliest signs of cognitive decline following a neurological or psychiatric insult or early in a disease process. However, in high-ability individuals, such decline is often difficult to detect early due to an individual's higher ceiling in most executive function measures. Many existing tasks assessing executive function are easily passed by individuals with higher ability, even when the individuals are impaired.

The present disclosures provides a system including a server computer configured to execute software logic within one or more testing software modules to generate and display, on one or more client machines (e.g., an examiner and examinee client device, described below), one or more tasks requiring user input responding to one or more decision points displayed on the client device and generated in association with the testing software modules.

The server computer may receive and automatically evaluate the user input, according to a plurality of data records stored in a database defining correct and incorrect responses, and the logic within the one or more testing software modules. Using the logic and data records, the server computer may generate a score for each test, wherein higher scores are determined according to a greater number of matches between the user input and the correct data records and logic, and lower scores are determined according to a lower number of matches between the user input and the correct data records and logic.

Thus, the disclosed system provides a new systematic assessment of executive functioning skills paradigms, based on a Delis-Kaplan Executive Functioning System (D-KEFS) test. The D-KEFS test has promise to detect and follow individuals at risk for cognitive decline following head trauma or neurological insult. It is non-invasive and inexpensive relative to positron emission tomography (PET) imaging, magnetic resonance imaging (MRI), and other current methods that are in intense development.

The disclosed embodiments of the D-KEFS assessment methodology provides a systematic assessment of individual executive functioning skills (e.g., those with head trauma). In addition to individual skill assessments, the disclosed embodiments may include single tasks that introduce multiple executive functions which the examinee must use simultaneously in order to complete the task correctly, thereby creating a higher-level condition to assess executive functioning by increasing the executive function load for examinees taking the D-KEFS test. In some embodiments, each added executive function may require a greater executive function load than the preceding task.

This allows assessment of individuals with higher ability, which may otherwise have passed the tasks including only individual executive functioning skills. That is, the addition of more difficult measures increases the sensitivity in higher-ability individuals. For example, in the trail making tests described herein, an examinee identifies and/or connects letters or numbers sequentially, or alternates between letters and numbers sequentially. In addition to this single task, examinees may be simultaneously required to change the pattern based on visual cues such as boxes around the letters or numbers, ignore additional distractions such as flashing graphics, and/or may be required to complete the task without the aid of visual feedback. Any combinations of these tasks may thereby increase the sensitivity of the assessment for individuals with higher abilities on task completion. This allows for earlier intervention or detection of decline at a time when intervention has a greater potential for slowing down a neurological insult or disease process.

Thus, the disclosed embodiments provide a systematic assessment of executive functioning skills. However, the testing environments may be perceived as sterile and may not represent daily life distractions (e.g., by administering neuropsychological tests in distraction-free, quiet, and controlled environments). In these sterile testing environments, individuals with higher abilities may easily pass existing tasks for assessing executive function, even when they are impaired (e.g., individuals having some brain injuries).

Clinicians, and other testing organizations, may also desire to determine whether individuals in testing situations are highly distractible in such testing accommodations and other testing situations (e.g., high stakes testing, such as the bar exam, the GRE, the SAT, etc.). The disclosed embodiments may therefore be used to determine whether or not a person is particularly distractible.

The distraction tasks in the disclosed embodiments build upon the previously tests disclosed below, creating a more ecologically-valid condition to assess executive functioning in an environment more similar to real-life settings and allow for more refined assessment of individuals with higher ability, the ecological validity of the tests generalizing to real world situations, as distractions are common in real-world settings. The additional requirement of completing the task while hearing and seeing alternate distracting stimuli will therefore increase the sensitivity of the assessment to individuals with higher abilities.

The distraction tasks may introduce stimuli that compete with the original task, to distract an examinee from accurately completing the task. The goal of the distraction is to make the examinee think incorrectly, thereby causing them to be distracted from the original objective within the task. Although simple auditory distraction or visual stimuli may be effective alone, the combination of visual and auditory distraction together, highly related to the task that the user is completing, produces a much higher effect, as shown in the disclosed embodiments.

Thus, as shown herein, the task may include both audio and visual distraction. For example, in the trail distraction tests disclosed below, an examinee may be required to conduct a series of tasks switching between numbers and letters, connecting dots in consecutive order while switching between a number sequence and a letter sequence (i.e., 1, A, 2, B, and so on). While the examinee is conducting the tasks, non-random distractions may be introduced, including auditory sounds and/or visual stimuli designed to mislead the examinee. For example, when a correct answer is the number 3 (which the examinee should select), they may hear the letter C being read aloud, which is also displayed on their testing screen, and so forth.

These distractors may also affect the time required to complete the tasks within the instructions. Thus, the distractors both slows down the user, and may cause them to make the wrong choice. The more general tests outlined herein may therefore be administered first, and then again with the distraction tasks added to the assessment. By using the same scoring rubric (described in detail below) the differences between the original test and the test with distractions may be analyzed, which may, in turn, create a more focused identification of the reason for the cognitive decline following head trauma or neurological insult, for example.

FIG. 1 illustrates a non-limiting example distributed computing environment 100, which includes one or more computer server computing devices 102, one or more client computing devices 106, and other components that may implement certain embodiments and features described herein. Other devices, such as specialized sensor devices, etc., may interact with client 106 and/or server 102. The server 102, client 106, or any other devices may be configured to implement a client-server model or any other distributed computing architecture.

Server 102, client 106, and any other disclosed devices may be communicatively coupled via one or more communication networks 120. Communication network 120 may be any type of network known in the art supporting data communications. As non-limiting examples, network 120 may be a local area network (LAN; e.g., Ethernet, Token-Ring, etc.), a wide-area network (e.g., the Internet), an infrared or wireless network, a public switched telephone networks (PSTNs), a virtual network, etc. Network 120 may use any available protocols, such as (e.g., transmission control protocol/Internet protocol (TCP/IP), systems network architecture (SNA), Internet packet exchange (IPX), Secure Sockets Layer (SSL), Transport Layer Security (TLS), Hypertext Transfer Protocol (HTTP), Secure Hypertext Transfer Protocol (HTTPS), Institute of Electrical and Electronics (IEEE) 802.11 protocol suite or other wireless protocols, and the like.

Figure 2:
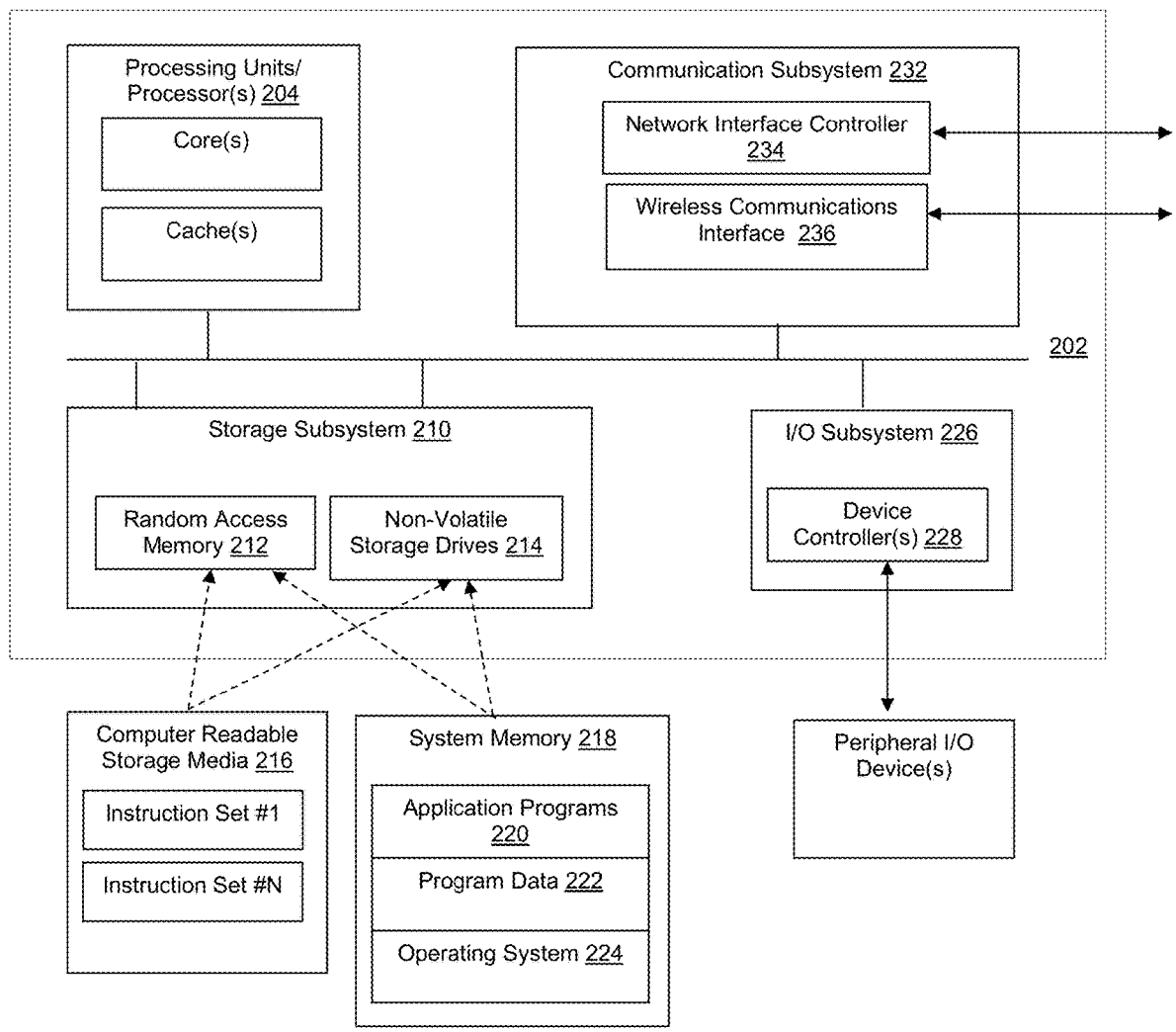
FIG. 2 illustrates a system level block diagram for administering and scoring multiple level executive functioning tests and tasks.

The embodiments shown in FIGS. 1-2 are thus one example of a distributed computing system and is not intended to be limiting. The subsystems and components within the server 102 and client devices 106 may be implemented in hardware, firmware, software, or combinations thereof. Various different subsystems and/or components 104 may be implemented on server 202. Users operating the client devices 106 may initiate one or more client applications to use services provided by these subsystems and components. Various different system configurations are possible in different distributed computing systems 100 and content distribution networks. Server 102 may be configured to run one or more server software applications or services, for example, web-based or cloud-based services, to support content distribution and interaction with client devices 106. Users operating client devices 106 may in turn utilize one or more client applications (e.g., virtual client applications) to interact with server 102 to utilize the services provided by these components. Client devices 106 may be configured to receive and execute client applications over one or more networks 120. Such client applications may be web browser based applications and/or standalone software applications, such as mobile device applications. Client devices 106 may receive client applications from server 102 or from other application providers (e.g., public or private application stores).

As shown in FIG. 1, various security and integration components 108 may be used to manage communications over network 120 (e.g., a file-based integration scheme or a service-based integration scheme). Security and integration components 108 may implement various security features for data transmission and storage, such as authenticating users or restricting access to unknown or unauthorized users, As non-limiting examples, these security components 108 may comprise dedicated hardware, specialized networking components, and/or software (e.g., web servers, authentication servers, firewalls, routers, gateways, load balancers, etc.) within one or more data centers in one or more physical location and/or operated by one or more entities, and/or may be operated within a cloud infrastructure.

In various implementations, security and integration components 108 may transmit data between the various devices in the content distribution network 100. Security and integration components 108 also may use secure data transmission protocols and/or encryption (e.g., File Transfer Protocol (FTP), Secure File Transfer Protocol (SFTP), and/or Pretty Good Privacy (PGP) encryption) for data transfers, etc.).

In some embodiments, the security and integration components 108 may implement one or more web services (e.g., cross-domain and/or cross-platform web services) within the content distribution network 100, and may be developed for enterprise use in accordance with various web service standards (e.g., the Web Service Interoperability (WS-I) guidelines). For example, some web services may provide secure connections, authentication, and/or confidentiality throughout the network using technologies such as SSL, TLS, HTTP, HTTPS, WS-Security standard (providing secure SOAP messages using XML encryption), etc. In other examples, the security and integration components 108 may include specialized hardware, network appliances, and the like (e.g., hardware-accelerated SSL and HTTPS), possibly installed and configured between servers 102 and other network components, for providing secure web services, thereby allowing any external devices to communicate directly with the specialized hardware, network appliances, etc.

Computing environment 100 also may include one or more data stores 110, possibly including and/or residing on one or more back-end servers 112, operating in one or more data centers in one or more physical locations, and communicating with one or more other devices within one or more networks 120. In some cases, one or more data stores 110 may reside on a non-transitory storage medium within the server 102. In certain embodiments, data stores 110 and back-end servers 112 may reside in a storage-area network (SAN). Access to the data stores may be limited or denied based on the processes, user credentials, and/or devices attempting to interact with the data store.

With reference now to FIG. 2, a block diagram of an illustrative computer system is shown. The system 200 may correspond to any of the computing devices or servers of the network 100, or any other computing devices described herein. In this example, computer system 200 includes processing units 204 that communicate with a number of peripheral subsystems via a bus subsystem 502. These peripheral subsystems include, for example, a storage subsystem 210, an I/O subsystem 226, and a communications subsystem 232.

One or more processing units 204 may be implemented as one or more integrated circuits (e.g., a conventional microprocessor or microcontroller), and controls the operation of computer system 200. These processors may include single core and/or multicore (e.g., quad core, hexa-core, octo-core, ten-core, etc.) processors and processor caches. These processors 204 may execute a variety of resident software processes embodied in program code, and may maintain multiple concurrently executing programs or processes. Processor(s) 204 may also include one or more specialized processors, (e.g., digital signal processors (DSPs), outboard, graphics application-specific, and/or other processors).

Bus subsystem 202 provides a mechanism for intended communication between the various components and subsystems of computer system 200. Although bus subsystem 202 is shown schematically as a single bus, alternative embodiments of the bus subsystem may utilize multiple buses. Bus subsystem 202 may include a memory bus, memory controller, peripheral bus, and/or local bus using any of a variety of bus architectures (e.g. Industry Standard Architecture (ISA), Micro Channel Architecture (MCA), Enhanced ISA (EISA), Video Electronics Standards Association (VESA), and/or Peripheral Component Interconnect (PCI) bus, possibly implemented as a Mezzanine bus manufactured to the IEEE P1386.1 standard).

I/O subsystem 226 may include device controllers 228 for one or more user interface input devices and/or user interface output devices, possibly integrated with the computer system 200 (e.g., integrated audio/video systems, and/or touchscreen displays), or may be separate peripheral devices which are attachable/detachable from the computer system 200. Input may include keyboard or mouse input, audio input (e.g., spoken commands), motion sensing, gesture recognition (e.g., eye gestures), etc.

As non-limiting examples, input devices may include a keyboard, pointing devices (e.g., mouse, trackball, and associated input), touchpads, touch screens, scroll wheels, click wheels, dials, buttons, switches, keypad, audio input devices, voice command recognition systems, microphones, three dimensional (3D) mice, joysticks, pointing sticks, gamepads, graphic tablets, speakers, digital cameras, digital camcorders, portable media players, webcams, image scanners, fingerprint scanners, barcode readers, 3D scanners, 3D printers, laser rangefinders, eye gaze tracking devices, medical imaging input devices, MIDI keyboards, digital musical instruments, and the like.

In general, use of the term "output device" is intended to include all possible types of devices and mechanisms for outputting information from computer system 200 to a user or other computer. For example, output devices may include one or more display subsystems and/or display devices that visually convey text, graphics and audio/video information (e.g., cathode ray tube (CRT) displays, flat-panel devices, liquid crystal display (LCD) or plasma display devices, projection devices, touch screens, etc.), and/or non-visual displays such as audio output devices, etc. As non-limiting examples, output devices may include, indicator lights, monitors, printers, speakers, headphones, automotive navigation systems, plotters, voice output devices, modems, etc.

Computer system 200 may comprise one or more storage subsystems 210, comprising hardware and software components used for storing data and program instructions, such as system memory 218 and computer-readable storage media 216.

System memory 218 and/or computer-readable storage media 616 may store program instructions that are loadable and executable on processor(s) 204. For example, system memory 218 may load and execute an operating system 224, program data 222, server applications, client applications, Internet browsers, mid-tier applications, etc.

System memory may further store data generated during execution of these instructions. System memory 218 may be stored in volatile memory (e.g., random access memory (RAM) 212, including static random access memory (SRAM) or dynamic random access memory (DRAM)). RAM 212 may contain data and/or program modules that are immediately accessible to and/or operated and executed by processing units 504.

System memory 218 may also be stored in non-volatile storage drives 214 (e.g., read-only memory (ROM), flash memory, etc.) For example, a basic input/output system (BIOS), containing the basic routines that help to transfer information between elements within computer system 200 (e.g., during start-up) may typically be stored in the non-volatile storage drives 214.

Storage subsystem 210 also may include one or more tangible computer-readable storage media 216 for storing the basic programming and data constructs that provide the functionality of some embodiments. For example, storage subsystem 210 may include software, programs, code modules, instructions, etc., that may be executed by a processor 204, in order to provide the functionality described herein. Data generated from the executed software, programs, code, modules, or instructions may be stored within a data storage repository within storage subsystem 210.

Storage subsystem 200 may also include a computer-readable storage media reader connected to computer-readable storage media 216. Computer-readable storage media 216 may contain program code, or portions of program code. Together and, optionally, in combination with system memory 218, computer-readable storage media 216 may comprehensively represent remote, local, fixed, and/or removable storage devices plus storage media for temporarily and/or more permanently containing, storing, transmitting, and retrieving computer-readable information.

Computer-readable storage media 216 may include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computer system 200.

By way of example, computer-readable storage media 216 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 216 may include, but is not limited to, Zip® drives, flash memory cards, universal serial bus (USB) flash drives, secure digital (SD) cards, DVD disks, digital video tape, and the like. Computer-readable storage media 216 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magneto-resistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 200.

Communications subsystem 232 may provide a communication interface from computer system 500 and external computing devices via one or more communication networks, including local area networks (LANs), wide area networks (WANs) (e.g., the Internet), and various wireless telecommunications networks. As illustrated in FIG. 2, the communications subsystem 232 may include, for example, one or more network interface controllers (NICs) 234, such as Ethernet cards, Asynchronous Transfer Mode NICs, Token Ring NICs, and the like, as well as one or more wireless communications interfaces 236, such as wireless network interface controllers (WNICs), wireless network adapters, and the like. Additionally and/or alternatively, the communications subsystem 232 may include one or more modems (telephone, satellite, cable, ISDN), synchronous or asynchronous digital subscriber line (DSL) units, Fire Wire® interfaces, USB® interfaces, and the like. Communications subsystem 236 also may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components.

In some embodiments, communications subsystem 232 may also receive input communication in the form of structured and/or unstructured data feeds, event streams, event updates, and the like, on behalf of one or more users who may use or access computer system 200. For example, communications subsystem 232 may be configured to receive data feeds in real-time from users of social networks and/or other communication services, web feeds such as Rich Site Summary (RSS) feeds, and/or real-time updates from one or more third party information sources (e.g., data aggregators). Additionally, communications subsystem 232 may be configured to receive data in the form of continuous data streams, which may include event streams of real-time events and/or event updates (e.g., sensor data applications, financial tickers, network performance measuring tools, clickstream analysis tools, automobile traffic monitoring, etc.). Communications subsystem 232 may output such structured and/or unstructured data feeds, event streams, event updates, and the like to one or more data stores that may be in communication with one or more streaming data source computers coupled to computer system 200.

The various physical components of the communications subsystem 232 may be detachable components coupled to the computer system 200 via a computer network, a FireWire® bus, or the like, and/or may be physically integrated onto a motherboard of the computer system 200. Communications subsystem 232 also may be implemented in whole or in part by software.

Due to the ever-changing nature of computers and networks, the description of computer system 200 depicted in the figure is intended only as a specific example. Many other configurations having more or fewer components than the system depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, a person of ordinary skill in the art will appreciate other ways and/or methods to implement the various embodiments.

Figure 3:
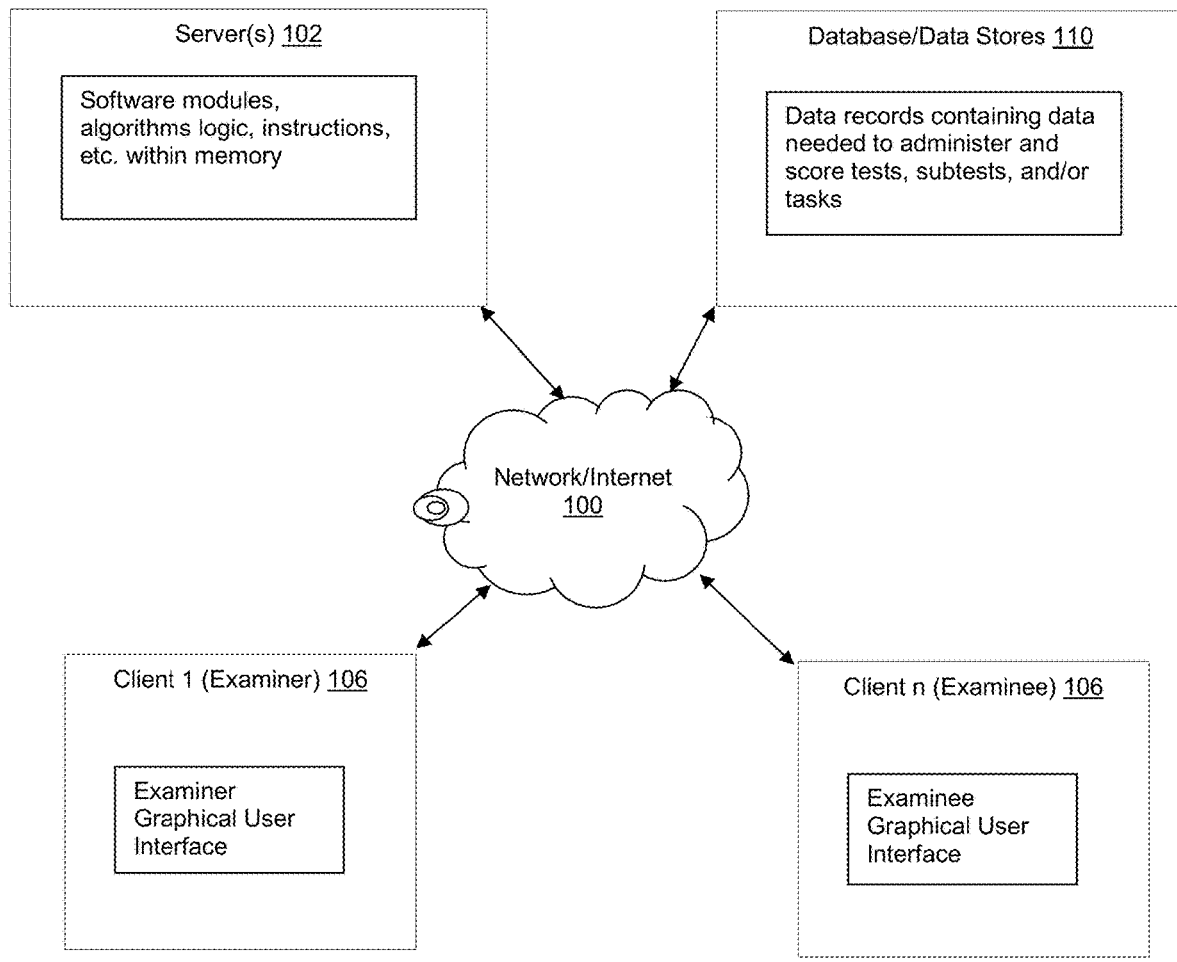
FIG. 3 illustrates a system level block diagram for administering and scoring multiple level executive functioning tests and tasks.

FIG. 3 shows a hardware and software environment in accordance with the present disclosure in which the disclosed tests may be given and the results calculated. One or more entities may operate one or more server hardware computing devices (server 102) in one or more data centers. Each server 102 may include one or more processors executing specific computer-executable instructions within a memory coupled to each server 102 and display the tests, subtests, and/or tasks themselves, as well as the results of the tests, to the administrator (examiner), and/or the user, test subject and/or patient (examinee). Thus, server 102 may include a computer or program that provides services to other computers, programs, or users over a computer network.

As noted above, the computer-executable instructions may be contained within one or more software modules. The disclosed embodiments do not limit the hardware computing devices that may run and execute such software and/or the computer-executable instructions within memory. For example, the software instructions may be run and executed on any combination of servers 102, and/or client hardware computing devices (clients 106). It should be understood, therefore, that although the disclosed embodiments refer to instructions, logic, and/or software modules being executed by server 102, the disclosed method steps may be executed by any combination of servers 102 and clients 106.

The disclosed embodiments may also include one or more data stores 110. Servers 102, clients 106 and data storage 110 may all be coupled via network 120. Data storage 110 may include any combination of content storage, databases, data tables, data records, and/or data fields storing data associated with the disclosed embodiments. These examples are non-limiting. For example, data storage 110 may be a relational or non-structured database, and/or may include any electronic document capable of storing data for a period of time, such as a spreadsheet, flat file, XML file, etc.

The software modules containing the algorithms, instructions, logic, etc. may execute the method steps disclosed herein, and in some disclosed embodiments, may be performed automatically without human interaction. As seen in FIG. 1, the disclosed environment may include one or more clients 106, and the one or more software modules may run on the server 102 or clients 106, which may include any computer or program that provides services to other computers, programs, or users either in the same computer or over a computer network 120. As non-limiting examples, the client 106 may include a laptop computer, a desktop computer or a mobile device, such as a mobile phone or a tablet computing device, which may connect wirelessly to the network 120.

In some embodiments, a first GUI may be provided for an examiner administrating a test, and a second GUI may be provided for an examinee taking the test. In these embodiments, both the examiner and examinee may each operate a client 106 (e.g., Client 1, Examiner client; Client n, Examinee Client), such as a tablet operated using a touch screen and/or a stylus. In these embodiments, seen in FIGS. 8, 9, and 11, an examiner GUI may include an electronic output providing the user with instructions for the exam, a first GUI control for monitoring the electronic input received from the user, and/or a second GUI control for demonstrating a correct response and an incorrect response to a prompt, as non-limiting examples.

The disclosed clients 106 may include GUIs allowing the examinee to interact with the tests and to display the results of the tests to the examiner and examinee. These GUIs may include graphical, textual, scanned and/or auditory information a computer program presents to the user, and the control sequences such as keystrokes, movements of the computer mouse, selections with a touch screen, scanned information etc. used to control the program. The commands received within the software modules, or other data, may be accepted using a field, widget and/or GUI control used in such interfaces, including but not limited to a text-box, text field, button, hyper-link, list, drop-down list, check-box, radio button, data grid, icon, graphical image, embedded link, etc.

In some configurations, the client 106 may receive input from an examinee. As non-limiting examples, this input may be used for the examiner or examinee to select a test, subtest, and/or task, for the examinee to acknowledge receipt of instructions, for an examiner or examinee to begin a practice or actual test, subtest, and/or task, for an examiner to pause a test and demonstrate errors or correct responses (e.g., identify correct or incorrect examinee responses or input during the test), for an examiner to stop an exam after a designated time period, etc., as disclosed in more detail below.

In some configurations, the input received by the client may be used to run calculations via a combination of server 102 and/or client(s) 106. For example, in administered tests described below, the test may be displayed, and the examinee's responses may be received via the client 106, but the display may be generated, the examinee's responses received, and the calculations to determine the results run on one or more servers 102 at a location remote from the client 106.

Software modules on server(s) 102 and/or client 106 may identify one or more data records within database 110 associated with tests, subtests and/or tasks selected by an examiner or examinee. Structurally, the database 110 may include a collection of data, and this data may be stored for a length of time, for example, with a secure server in the cloud, providing access to the generated data as desired.

As non-limiting examples, associated data records may include data records containing algorithms, rules, calculations, textual or multimedia (e.g., image or audio) data needed for: instructions displayed on client 106 and/or read by the examiner for practice tests or conditions; images, numbers, letters, boxes, colors, layout, etc. necessary for practice and/or actual tests and/or tasks; GUI controls, images, characters or character strings, etc. for practice or actual tests and/or tasks; timers for both practice and actual tests and/or tasks; type of incorrect response (e.g., sequencing or set loss errors); mapping (e.g., sequences, layout, connecting lines, etc.) for correct and incorrect answers at each decision point within example and actual tests and/or tasks; responses and/or notifications to be displayed to examinees upon correct and incorrect input; scoring paradigms for each test and/or task; actual user scores according to the scoring paradigms; one or more cognitive declines, neurological insults, and/or early stage diseases; an association between the one or more cognitive declines, neurological insults and/or early stage diseases, a predetermined threshold, and one or more of the user scores below which each cognitive decline, neurological insult and early stage disease may be identified; etc.

For each test, software modules on server 102 and/or client 106 may generate a GUI display (e.g., a web page or a client application GUI), for authenticating the examiner and/or the examinee. This GUI may be displayed on the client computer(s) 106 (e.g., the examiner and/or examinee's tablet computer). The examiner and/or examinee may be authenticated to the disclosed software modules, possibly using a username and password created by the examiner and/or examinee in association with an examiner and/or examinee account stored in database 110. Data for the examiner and/or examinee account may include, as non-limiting examples, the username and password, and in some embodiments, data regarding the cognitive functions being tested, examinee history (e.g., previous test scores, reason for test, etc.), tests that the examiner has deemed prudent to be administered to the examinee, etc.

Turning now to FIGS. 4-17, the disclosed D-KEFS test may include a battery of subtests (e.g., 9 subtests each with 1 or more tasks, also referred to as conditions or trials), each of which may be associated in the database 110 with a function skill used to demonstrate a cognitive ability of an examinee. These cognitive abilities within the tasks and function skills may be scored to determine the user's ability to respond to various instructions, and the resulting scores may be used to identify a user's cognitive decline, neurological insult, early stage disease, etc.

In some configurations, an examinee may be a test subject that is part of a clinical trial. The disclosed system may be part of an initial screen at the sites administering the clinical trial. In these configurations, the examiners (e.g., clinicians and/or doctors) may be screening the subject for declines in executive functions, one of the earliest signs of cognitive decline following a neurological insult or early in a disease process. The examinee may come to the testing site and interact with a computer, mobile device, etc. in an environment controlled by the examiner.

The 9 subtests, as well as their tasks are described in detail below, and may include, as non-limiting examples: Trail Making, Verbal Fluency, Design Fluency, Color Word Interference, Tower, Social Sorting, Derby, Prosody Word Interference, and Grocery List.

As noted above, each of the tests, subtests and/or tasks may be associated with a function skill used to demonstrate the cognitive ability of the examinee. In the subtests and tasks described below, these function skills may include a list of function skills within an executive function domain. Database 110 may store a plurality of task data for each executive function domain, and each executive function domain name may be further associated with and represent a function skill demonstrating a cognitive ability of the user.

As non-limiting examples, the executive function domains may include: Cognitive/Behavioral Control, Planning, Cognitive Flexibility (which may include a dual-level, triple-level, or other multi-level switching task), Inhibitory Control, Self-Monitoring, Rule Violations, Behavioral Productivity (Initiation), Risk-Taking Control, Affect Perception, and Emotion Regulation, each of which will be described as associated with the tasks described in greater detail below.

Examples of these types of tasks are as follows: (a) dual-level task: the Inhibition/Switching Condition of the Color-Word Interference Test; (b) triple-level task: the Switching/Distraction condition of the Color-Word Interference Test or the Complex Switching Condition of the Trail Making Test; (c) Cognitive/Behavioral Control: the Derby Test; (d) Cognitive Flexibility: all switching conditions of the Trail Making Test, Color-Word Interference Test, Design Fluency Test, Verbal Fluency Test, Prosody-Word Interference Test, and Social Sorting Test; (e) Inhibitory Control: The Color-Word Interference Test and the Prosody-Word Interference Test; (f) Self-Monitoring (all tests); (g) Rule Violations: all tests except for The Derby Test; (h) Behavioral Productivity (Initiation): all conditions of the Design Fluency Test, the Verbal Fluency Test, and the Tower Test; (i) Risk Taking Control: The Derby Test; (j) Affect Perception: the Social Sorting Test and Prosody-Word Interference Test; and (k) Emotional Regulation (The Derby Test and Social Sorting Test).

To administer the various subtests and tasks, server 102 may authenticate each examiner and/or examinee, and may further render and transmit, for display on the examiner or examinee's client 106, a GUI (not shown) for selecting at least one of the subtests and/or tasks for the examinee. Upon receiving the selection, one or more software modules on server 102 may identify and select all data records in database 110 associated with the selected task (e.g., by identifying a unique identifier within all related data records for the selected task). The software modules may then analyze the data stored within the data records, including any data, logic, instructions, rules, content, correct or incorrect answers, scoring data, etc., relevant to the selected test as disclosed above.

Figure 11:
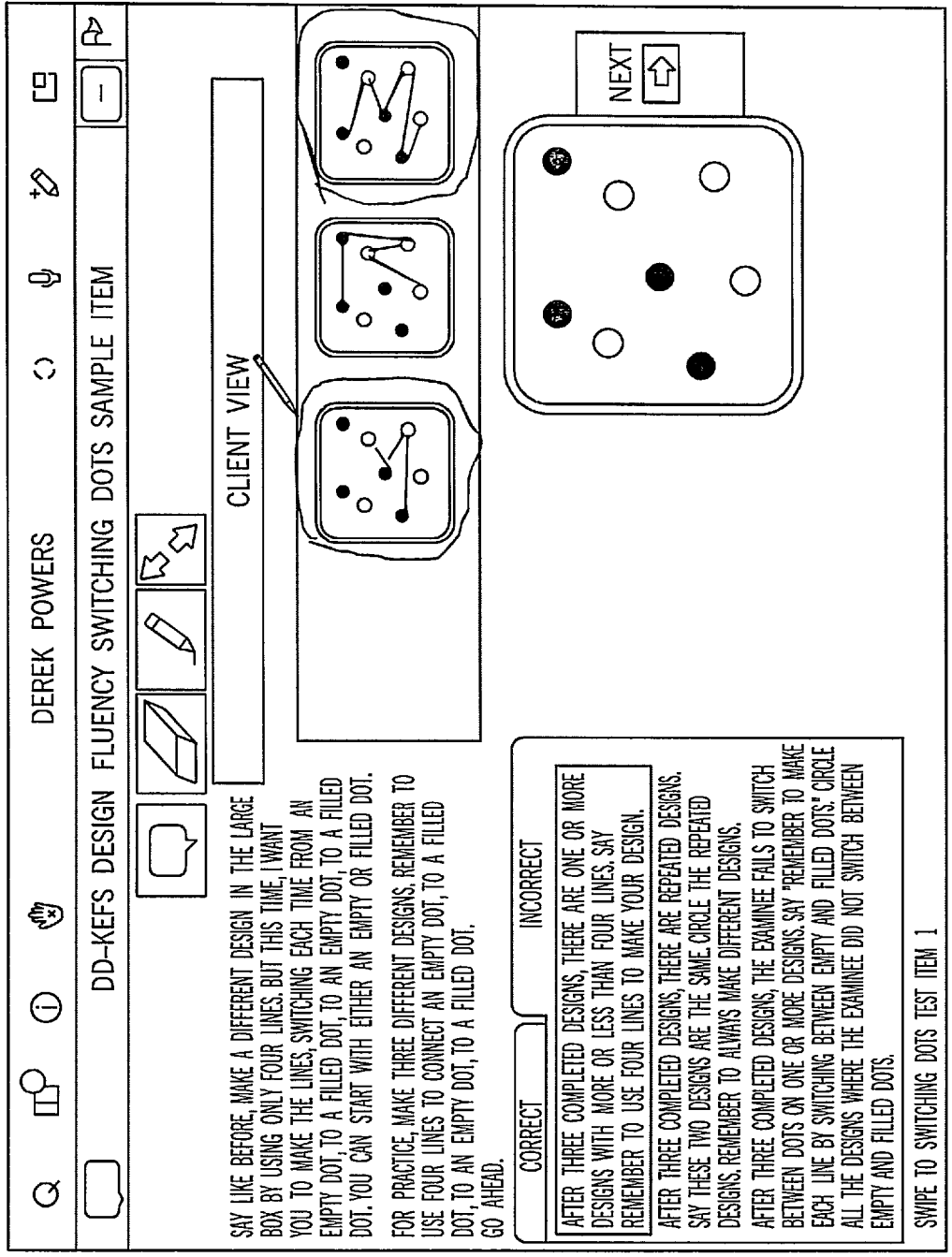
FIG. 11 illustrates an example user interface for administering and scoring multiple level executive functioning tests and tasks.
Figure 12:
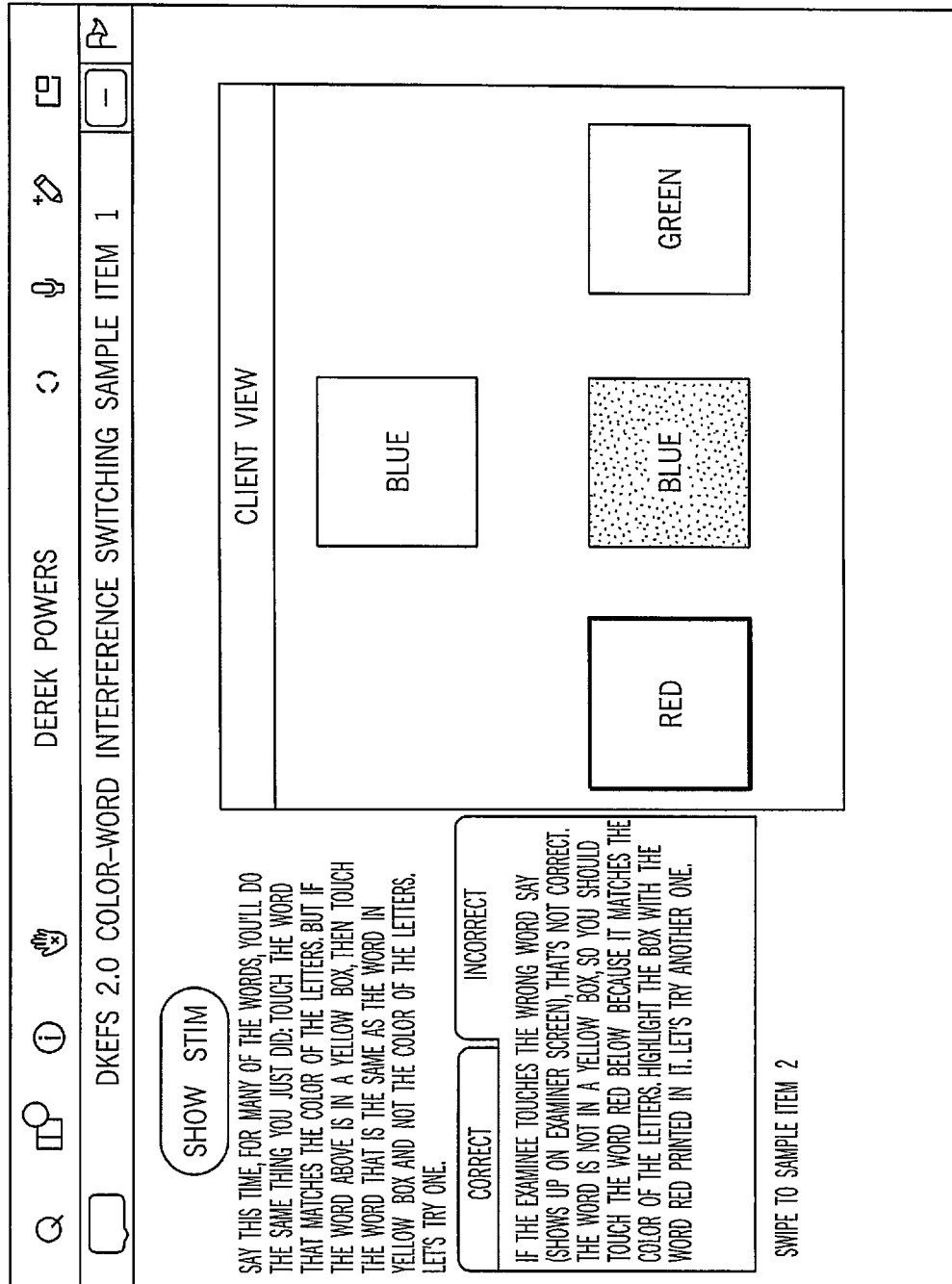
FIG. 12 illustrates an example user interface for administering and scoring multiple level executive functioning tests and tasks.
Figure 14:
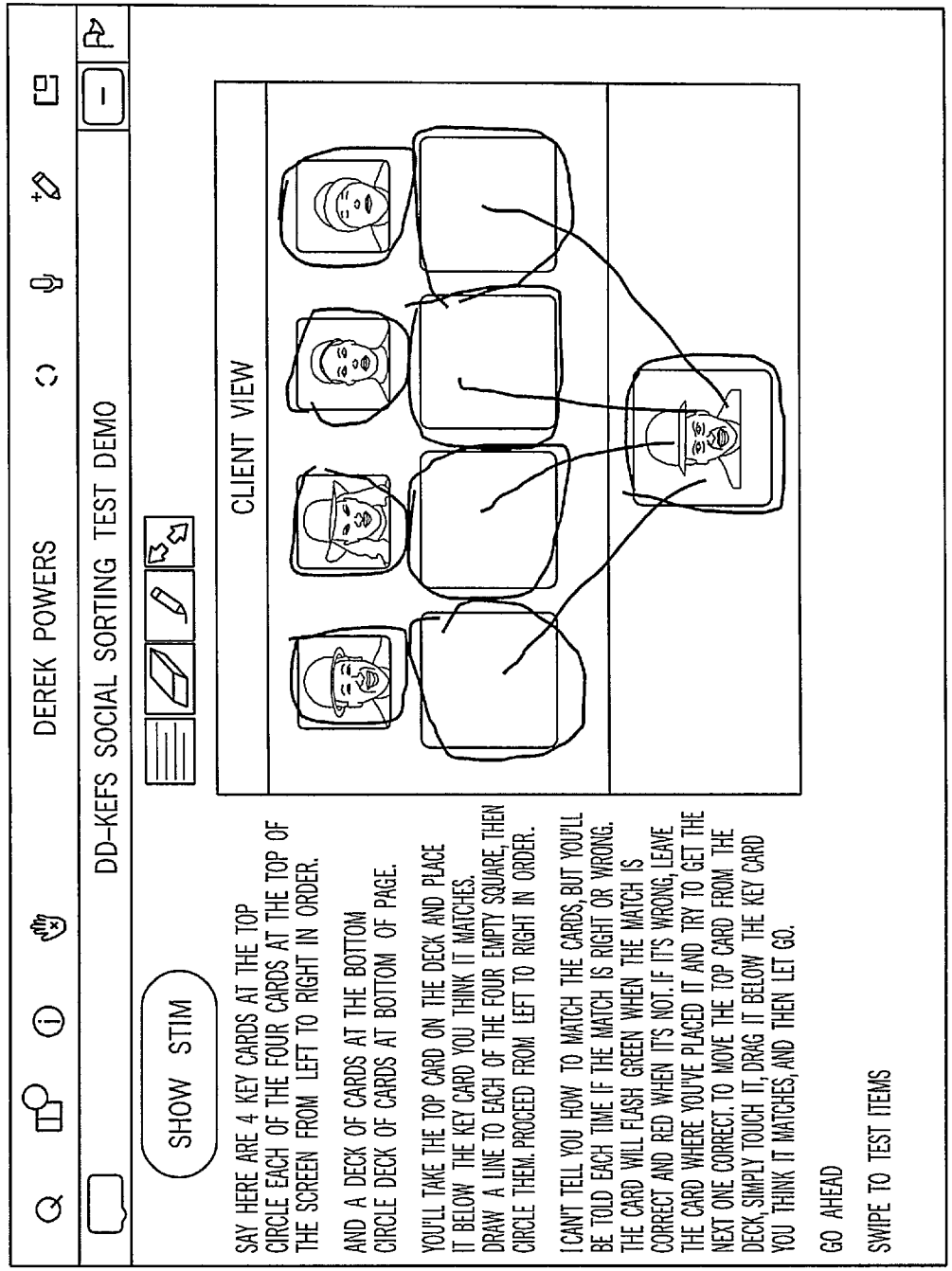
FIG. 14 illustrates an example user interface for administering and scoring multiple level executive functioning tests and tasks.

Server 102 may then render/generate one or more GUIs displaying the selected subtest and/or task content. The one or more GUIs may encode any combination of: a first series of user interface objects comprising a first sequence or a plurality of character string descriptions; a second series of user interface objects comprising a second sequence or a plurality of user interface characteristics; and at least one visual indicator display object requiring a switch between the first series of user interface objects, and the second series of user interface objects;

In the non-limiting examples seen in FIGS. 11, 12, and 14, server 102 may render two separate GUIs, one for the examiner and one for the examinee. For example the examiner or examinee GUI may be displayed on the examiner client 106 (Client 1, e.g., a touch sensitive tablet using a stylus) or examinee client 106 (Client n, a second touch sensitive tablet using a stylus) respectively.

The non-limiting-example examiner GUIs in FIGS. 11, 12, and 14 demonstrate that the examiner GUI may render instruction data associated with the selected subtest and/or task, possibly including instructions to be read and conveyed to the examinee regarding how the test is to be administered. In embodiments where the examinee is using a single tablet, this instruction data, as well as the displayed correction data described below, may be displayed or otherwise presented to the examinee (e.g., via display on a display screen or through audio instruction from an audio file, etc.). As a non-limiting example, the instruction data may include data indicating a timer for each practice or actual test or task, and the instructions may direct examinees to work as fast as they can within these time constraints without making mistakes. The examinee may acknowledge (possibly via the examinee GUI) that the instructions are understood, and in response, server 102 may select the data records associated in the database with a practice test (e.g., graphics, text, correct/incorrect responses, notifications, examples, etc.), and may generate and render a practice test GUI used to acclimate the examinee to the timing and tasks of the subtest.

After receiving and reviewing the instruction for the practice test, the examinee may enter a user input indicating that the instructions are understood and the practice test should begin. The timer may then be started, either at the conclusion of the instructions, or when the examinee acknowledges the instructions to begin. As non-limiting examples, the timer may include any range from 15 to 210 seconds, though other timer ranges are contemplated. Regarding the timer, the software modules may compare the examinee's elapsed time with the timer data stored in database 110 for the subtest/task. If the elapsed time is greater than the timer data for the test or task, the software modules may automatically terminate the practice test, or generate an alert that the elapsed time is greater than the timer data.

Client 106 may receive and decode task input (e.g., examinee responses to the task conditions) from the examinee client 106, as input by the examinee. This user input may be forwarded to and utilized by the algorithms disclosed herein for calculating and displaying the results of the user input, in real time, and/or may be stored within the database 110, possibly as one or more data records associated with the examinee.

Each practice test and actual test may include various errors. As non-limiting examples, such errors may include sequencing errors or set loss errors. Sequencing errors may include, as non-limiting examples, a user touching or creating a path between objects in the incorrect order (e.g., touching or drawing a line between 1 and 3 instead of 1 and 2). Set loss errors may include errors where data is missing (e.g., user does not respond to a prompt in an appropriate manner).

In some embodiments, the system may generate prompts during the practice or actual test for the examiner, stored in the database. These prompts may be provided in response to the examinee's input. A combination of software instructions executed by the software modules running on server 102 and/or client 106 may receive the user input from each task, and analyze the received input by comparing the examinee's responses against the correct answers to responses to task prompts (possibly stored as data records in database 110) in order to determine if the received answers match the correct answers. The software modules may analyze the received input and generate displays or other output including a notification to the user that the user input is correct or incorrect (e.g. "that is/is not correct"), or that it is incorrect (e.g., "that is incorrect because . . . "), and directing the examinee how to proceed (e.g., "try again from . . . "). The subject may then be presented with a GUI indicating that the user input included correct or incorrect responses for the practice test.

As noted above, as the examinee progresses through the practice test, the examinee's input may be analyzed and displayed in real time. This client view may be transmitted from the client GUI to server 102, which may render the user input within the client view GUI control, and transmit the rendering to the examiner GUI in real time, thereby allowing the examiner to view the examinee's responses and other input in real time. In embodiments where this input is displayed within a client view GUI control on the examiner GUI (e.g., FIGS. 7, 8, and 10) the examiner may acknowledge and reinforce correct answers.

As seen in FIGS. 11, 12 and 14, the examiner GUI may also include instructions for responding to responses input by the examinee. For example, FIGS. 7-8 each include a "correct" and "incorrect" tab with instructions for the examiner to respond according to the examinee inputting a correct or incorrect response, respectively. In some embodiments, if the user input is incorrect, the screen may freeze (e.g., the examinee is unable to make any more responses beyond the error), the examiner or software may create an X or other visual cue that the selection or line was incorrect, and/or the practice test may be otherwise paused while the software or examiner provides feedback. Using these tools, the examiner may monitor the input by the examinee for practice and actual tests.

The examiner GUI may further control the examinee interface, so that if the examinee makes a mistake, the software or examiner may pause the practice test, and provide feedback (e.g., highlighting the mistake) instructing the examinee that the selection was incorrect, and the software or examiner may demonstrate a correct response on the client view. In some embodiments, the examiner and/or software may, for example: highlight correct letters, numbers, text, boxes, paths, selections, etc. and create lines showing proper paths, order, selections, etc. The instructions may then direct the examiner (possibly using highlights or other visual cues) to direct the examinee to begin again from the last correct input/decision point.

In some embodiments, the examiner's role may be automated. Thus, as non-limiting examples, the instructions may be displayed on the client GUI, the demonstration may be displayed on the client GUI, and the server may monitor and correct the examinee during the practice exams.

During the actual test, the timer may be started, possibly after the examinee acknowledges the start, selects the first selection, or responds to prompts or decision points. The examinee may continue working through the time provided by the timer without interruption from the examiner.

Multi-level subtests and/or tasks, as described below, may be administered via the disclosed system. Some of these subtests and/or tasks may incorporate cognitive flexibility, meaning that the user may incorporate compound/complex instructions and working memory, for example. This may improve the sensitivity and specificity of the scores for each task, subtest, or overall test for each examinee, and may further improve the ability to identify the cognitive decline, neurological insult, early stage disease, etc., since performance on these tasks would be expected to reflect the integrity of both the cognitive functions/abilities, neurological integrity, lack of disease, etc. and memory neural systems. In addition to collecting input from the subject, additional information may be collected. For example, in addition to determining whether or not the subject provided correct user input, the system may be configured to determine the amount of time it takes the subject to respond to the prompt. The system may record an examinee's response time to determine how long it takes them to make a decision, for example.

Thus, server 102 may combine the dual-level, triple-level, or other multi-level tasks, combining multiple various tasks in order to test executive function domains, which may allow for additional testing or tracking components that requires the examinee to, for example, determine if they switch or continue with the same sequence. In the example embodiments described below, an examinee may be required to alter their behavior according to the at least one visual indicator requiring a switch. For example, the visual indicator may include: a box displayed around a number, letter, dot, etc.; a change in a character string or font color of a character string; an outline or background of a box displaying the test data; etc. In other words, the dual, triple, and other multiple-level tasks indicated by the visual indicator build upon the existing D-KEFS testing components to create a higher-level condition to assess executive functioning by requiring multiple skills to be used at the same time.

At the end of each task, subtest, and/or the overall test battery, after the examinee has completed all tasks, and/or at the conclusion of the timer, the software modules may be configured to calculate the test results based on the examinee's input. For example, the electronic input provided by the examinee may be compared with the correct answers stored in association with the selected subtest and/or task within data records in the database. The software modules may then run calculations to analyze the examinee's answers and generate a score including the number of correct answers for each or all of the tasks for each of the subtests. The correct or incorrect answers may be calculated according to the electronic input matching, or failing to match, a correct response associated in database 130 with a task data defining a function skill demonstrating a cognitive ability of the examinee.

The final score may be compared with a threshold number, and if the score is below the threshold number, one or more of a cognitive decline, a neurological insult, or an early stage disease may be identified as associated in the database with the score below the threshold number. The software modules may then store the results in database 110.

Thus, the disclosed system software may determine whether the user has been a good or poor performer in relation to cognitive decline, a neurological insult, or an early stage disease. The software may make this determination via the algorithms disclosed herein, and may generate the results of the tests and the interpretation of these test results (e.g., whether or not the subject a poor performer, and therefore at risk of neurodegenerative disease) in real time. The results of the tests and interpretation of the results may then be displayed as a report to the examiner (e.g., to a physician). The examiner may then present and contextualize the result for the examinee, similar to how this is currently done with radiology and LP results.

Figure 4:
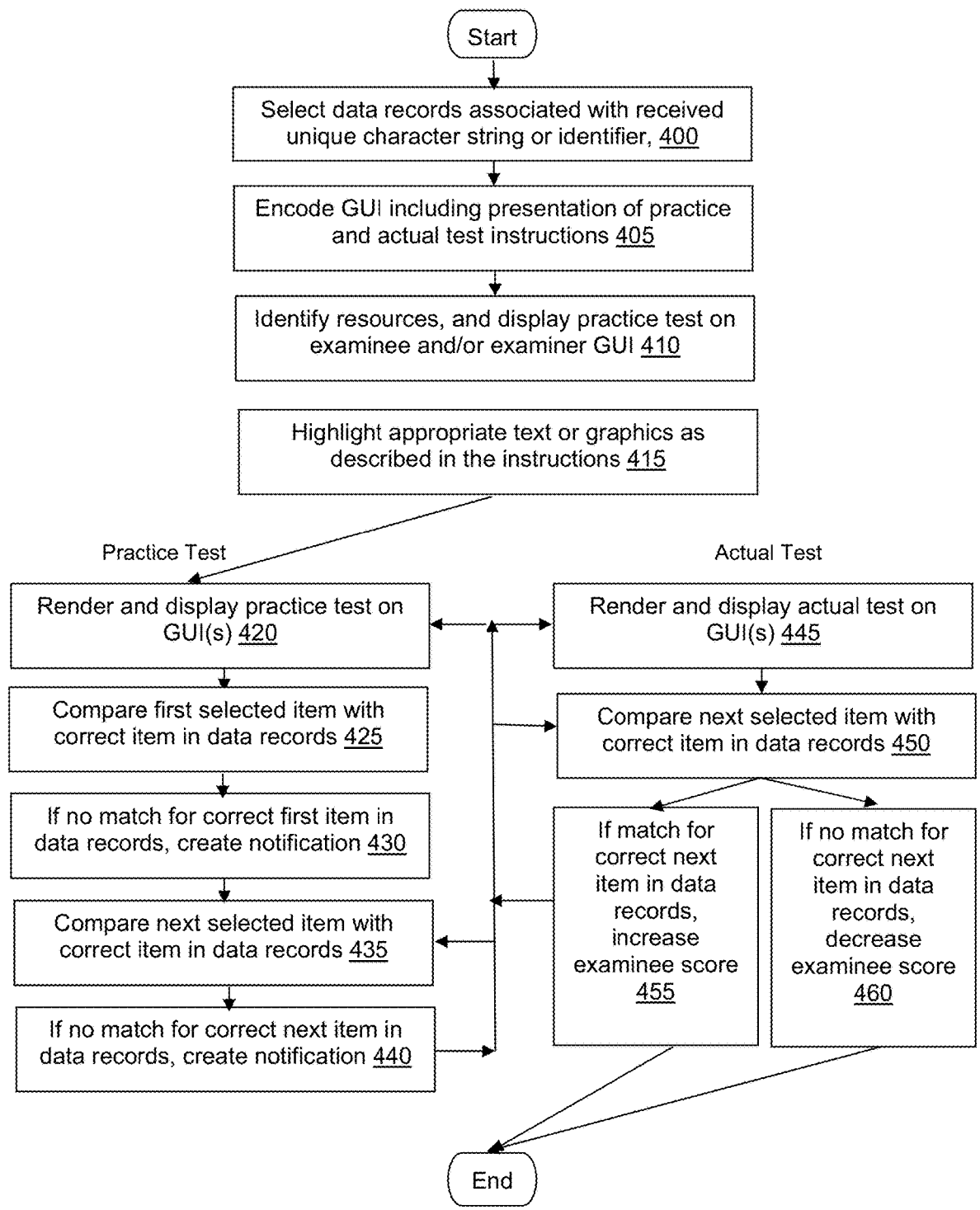
FIG. 4 illustrates a flow diagram for administering and scoring multiple level executive functioning tests and tasks.

Turning now to FIG. 4, a series of method steps is shown, which apply to the tests, subtests, and/or tasks requiring actions taken in sequential order, possibly with additional instructions, as demonstrated in FIGS. 7-11, 13, and 17-19. In these embodiments, the GUI on the client 120 may receive user input requesting the Trail Making, Design Fluency, Tower, or Grocery List subtests and/or tasks as demonstrated in FIGS. 7-11, 13, and 17-19.

In step 400, server 102 may identify the selected test, subtest, and/or task, possibly by receiving from the GUI a unique identifying character string (e.g., "Trail Making/Number Sequencing," "Design Fluency/Mixed Dots," "Tower," "Grocery List," etc.) or a unique alphanumeric identifier for the selected test, subtest, or task. Server 102 may then execute a database query to identify the selected test, subtest, or task by matching the unique identifying character string or alphanumeric identifier received from the GUI with a test, subtest, or task data record within the database 110. Server 102 may then select all additional data records associated in database 110 with the selected test, subtest, and/or task (e.g., by selecting all data records including the unique character string or alphanumeric identifier for the test, subtest, and/or task).

In step 405, server 102 may use the data stored in these data records, as well as logic and rules within the software modules running on server 102 and/or client 106, to encode and render one or more GUIs to be transmitted to, and displayed on, client(s) 106. The GUI generated and rendered from the data, logic, and rules may include instructions for the examinee to take the practice and actual tests. In embodiments where server 102 generates and renders both an examiner GUI and an examinee GUI displayed within a client view on the examiner GUI, server 102 may generate and render the instructions on the examiner GUI for the examiner to read out loud to the examinee. In embodiments including only the examinee GUI, server 102 may generate and render the instructions on the examinee GUI, or generate an audio output providing the instructions to the examinee.

In step 410, the GUI generated and rendered from the selected data may include one or more practice tests. Server 102 may analyze the data from the selected data records and/or the logic and rules in the software modules in order to determine the layout for the practice test. For example, the data, logic, and/or rules may require that: the Trail Making tasks provide multiple sequential number and letter graphics or text distributed in random order across the GUI, some of which may be surrounded by boxes, or a sampling of empty dot graphics, with dots labeled Start and Finish; the Design Fluency tasks provide multiple filled and empty dot graphics distributed in random order across the GUI, and a "next" GUI control for creating multiple designs, which causes the server to generate and display another examinee GUI control with a different set of filled and empty dot graphics; the Tower tasks provide multiple peg graphics and one or more chip graphics to be placed on, and moved between, the pegs; and the Grocery List tasks provide one or more grocery list graphics displayed at the top of the examinee GUI to be collected, multiple grocery item graphics (some matching the grocery list items) distributed among one or more aisle graphics, a grocery cart graphic to be moved among the grocery items/aisles, and a checkout graphic. Server 102 may identify, from the selected data, logic, or rules, one or more required text or graphical elements (e.g., filed or empty dot graphics, numbers and letters to be displayed within the graphics, box graphics to be placed around the dot graphics, pegs, chips, grocery items, aisles, grocery cart, checkout, etc.) and render and display these items on the examinee (and/or client view of the examiner's) GUI according to the data, logic, and/or rules.

In step 415, using these rendered GUIs, server 102 and/or client 106 may highlight the appropriate text or graphics as they are described in the instructions (e.g., highlighting each number in order, or an example line generated between numbers in order; highlighting a correctly drawn line to create a design; highlighting a correct chip to be placed on a correct peg; highlighting a correct path between the shopping cart and the first item in the shopping list; etc.).

In step 420, after the instructions for the test, subtest, and/or task are provided and demonstrated, server 102 may render and display a first practice test on the one or more GUIs. The examinee GUI may receive user input selecting a first displayed item, and transmit the user input to server 102 for analysis. In step 425, server 102 may compare the first selected item with a correct first selected item defined within the data records, logic, and/or rules (e.g., a dot containing 1 or A, a first designated chip on a first designated peg, selection of the grocery cart to move towards the first grocery item, etc.). In step 430, if the selected first item, and the first item in the data records, logic, and/or rules do not match, server 102 may automatically generate, render, and display a notification that the first item was not correct, and to try again (e.g., provide instructions "that is not correct, please begin again with 1, A, this chip or peg, the grocery cart, etc.").

In step 435, the examinee GUI may then receive user input selecting a next sequential item (e.g., a user input selecting a dot containing 2 after 1, or B after A, or a line connecting 1 to 2 or A to B; a user input connecting an empty dot to a filled dot within a design; a user input selecting a chip to move to a different peg; a user input moving the grocery cart to a first item in the grocery list; etc.), and transmit the user input to server 102 for analysis. Server 102 may compare the selected next sequential item with a correct next sequential item defined within the data records, logic, and/or rules (e.g., 2 follows 1 or B follows A; an empty dot follows a filled dot; a specific chip should be moved in order to a specific peg; a grocery item closest to the grocery cart should be selected first, etc.). In step 440, if the selected next sequential item, and correct next sequential item defined in the data records, logic, and/or rules do not match, server 102 may automatically generate, render, and display a notification that the selected next sequential item was not correct, and to try again (e.g., provide instructions "that is not correct, please begin again with 1, A, this chip or peg, the grocery cart, etc."). In some embodiments, the examinee GUI may highlight then incorrect sequential and/or a correct sequential selection.

After the practice test is complete, the examinee or examiner GUI may receive user input requesting another practice, and server 102 and client(s) 106 may repeat the steps above to generate a new practice test. After all practice tests are complete, the examinee or examiner GUI may receive user input requesting the actual test, and in step 445, server 102 and client(s) 106 may repeat the steps above to generate, render, and display the requested actual test.

However, during the actual test, after comparing the selected next sequential item with a correct next sequential item defined within the data records, logic, and/or rules (Step 450), if the selected next sequential item, and correct next sequential item defined in the data records, logic, and/or rules match, in step 455, server 102 may automatically increase the examinee's score. If the selected next sequential item, and correct next sequential item defined in the data records, logic, and/or rules do not match, in step 460, server 102 may automatically decrease examinee's score. Once the actual test is complete, or the timer has run out, server 102 may automatically generate a final score for the examinee, and identify potential cognitive decline, as disclosed above.

Figure 5:
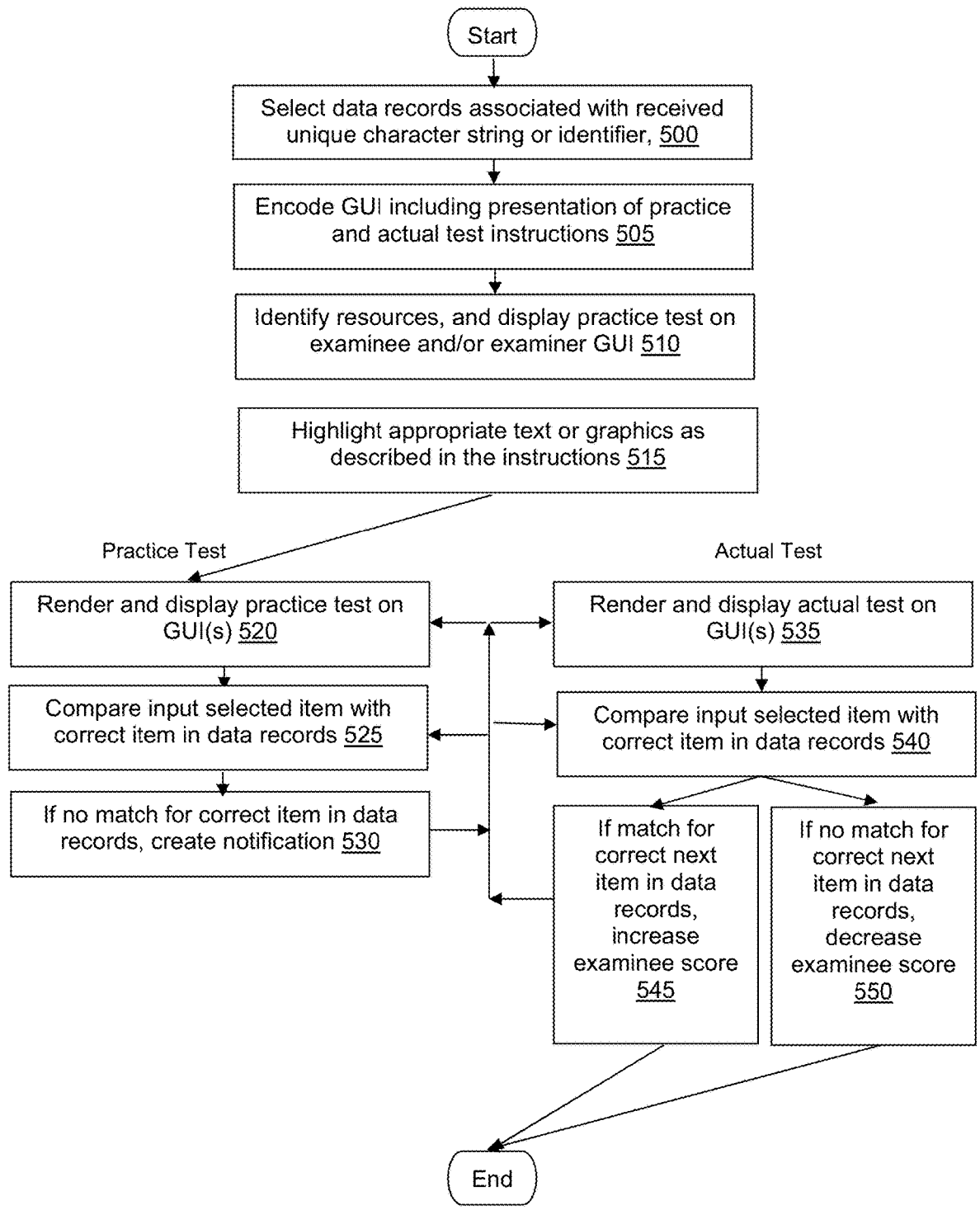
FIG. 5 illustrates a flow diagram for administering and scoring multiple level executive functioning tests and tasks.

Turning now to FIG. 5, a series of method steps is shown, which apply to the tests, subtests, and/or tasks requiring actions taken matching a prompt provided through the GUI(s) with a character string and/or graphic matching an element of the prompt (e.g., matching character string, color, tone of voice, etc.), possibly with additional instructions, as demonstrated in FIGS. 10, 12, and 13-14 and 18-19 In these embodiments, the GUI on the client 120 may receive user input requesting the Verbal Fluency, Social Sorting, Color Word Interference, Prosody Word Interference, or Derby subtests and/or tasks as demonstrated in FIGS. 12, and 14-16 and 18-19 (Verbal Fluency subtest not shown).

In step 500, server 102 may identify the selected test, subtest, and/or task, possibly by receiving from the GUI a unique identifying character string (e.g., "Verbal Fluency/ Letter Fluency," "Social Sorting/Emotion Sorting," "Color Word Interference/Color Identification," "Prosody Word Interference/Emotion Naming," "Derby," etc.) or a unique alphanumeric identifier for the selected test, subtest, or task. Server 102 may then execute a database query to identify the selected test, subtest, or task by matching the unique identifying character string or alphanumeric identifier received from the GUI with a test, subtest, or task data record within the database 110. Server 102 may then select all additional data records associated in database 110 with the selected test, subtest, and/or task (e.g., by selecting all data records including the unique character string or alphanumeric identifier for the test, subtest, and/or task). Step 505 may proceed in a manner analogous to step 405 described above.

In step 510, the GUI generated and rendered from the selected data may include one or more practice tests. Server 102 may analyze the data from the selected data records and/or the logic and rules in the software modules in order to determine the layout for the practice test. For example, the data, logic, and/or rules may require that: the Verbal Fluency tasks provide multiple letters and/or categories (either for display or as an audio output), and a GUI control for receiving user input; the Social Sorting tasks provide a series of key card graphics, several graphics representing a card deck, and a series of GUI controls for receiving a user input attempting a match of a card in the key card graphics and a card from the card deck; the Color Word Interference tasks provide one or more boxes, which may be displayed in different/offset positions, including a color, a background color, a character string, a font color, and/or a border color, and a series of boxes each including a character string describing a match to the color, the background color, the character string, or the font color; the Prosody Word Interference tasks provide multiple audio outputs stating a word and/or stating it in a tone of voice, and multiple boxes, each including a character string describing a match to the word and/or the tone of voice; and the Derby tasks provide a racetrack, horses and jockeys, monetary selection boxes, a finish line, and a running total of money. Server 102 may identify, from the selected data, logic, or rules, one or more required text or graphical elements (e.g., letters and/or categories output or displayed and a GUI control for user input, cards and card slots for matching, series of boxes with character strings, possibly with a specific background, border, or font color, racetrack and money graphics, etc.) and render and display these items on the examinee (and/or client view of the examiner's) GUI according to the data, logic, and/or rules. In step 515, using these rendered GUIs, server 102 and/or client 106 may highlight the appropriate text or graphics as they are described in the instructions (e.g., highlighting a letter or category to input matching character strings, or a card in a card deck matching specific key cards, or each character string in boxes matching a correct character string, audio output, tone of voice, background color, font color, etc.).

In step 520, after the instructions for the test, subtest, and/or task are provided and demonstrated, server 102 may render and display a first practice test on the one or more GUIs, possibly including required audio output. The examinee GUI may receive user input including a selection of character strings matching a letter and/or category, a card in the card deck matching a key card, a box including a character string matching the audio output, a tone of voice in the audio output, a background color, character string, font color, displayed in another box, a selected horse and jockey etc., and transmit the user input to server 102 for analysis. In step 525, server 102 may compare the selected item with a correct selected item defined within the data records, logic, and/or rules (e.g., an input matching the correct letter or category, a card in the card deck matching a card in the key cards, a selected box matching the character string, font color, or background color of another box, the winning horse and jockey, etc.). In step 530, if the selected item, and the item in the data records, logic, and/or rules do not match, server 102 may automatically generate, render, and display a notification that the selected item was not correct, and to try again (e.g., provide instructions "that is not correct, please make another selection or begin again").

After the practice test is complete, the examinee or examiner GUI may receive user input requesting another practice, and server 102 and client(s) 106 may repeat the steps above to generate a new practice test. After all practice tests are complete, the examinee or examiner GUI may receive user input requesting the actual test, and in step 535, server 102 and client(s) 106 may repeat the steps above to generate, render, and display the requested actual test.

However, during the actual test, after comparing the input selected item with a correct input selected item defined within the data records, logic, and/or rules (Step 550), if the input selected item, and correct selected item defined in the data records, logic, and/or rules match, in step 545, server 102 may automatically increase the examinee's score. If the input selected item, and correct selected item defined in the data records, logic, and/or rules do not match, in step 560, server 102 may automatically decrease examinee's score. Once the actual test is complete, or the timer has run out, server 102 may automatically generate a final score for the examinee, and identify potential cognitive decline, as disclosed above.

Figure 6:
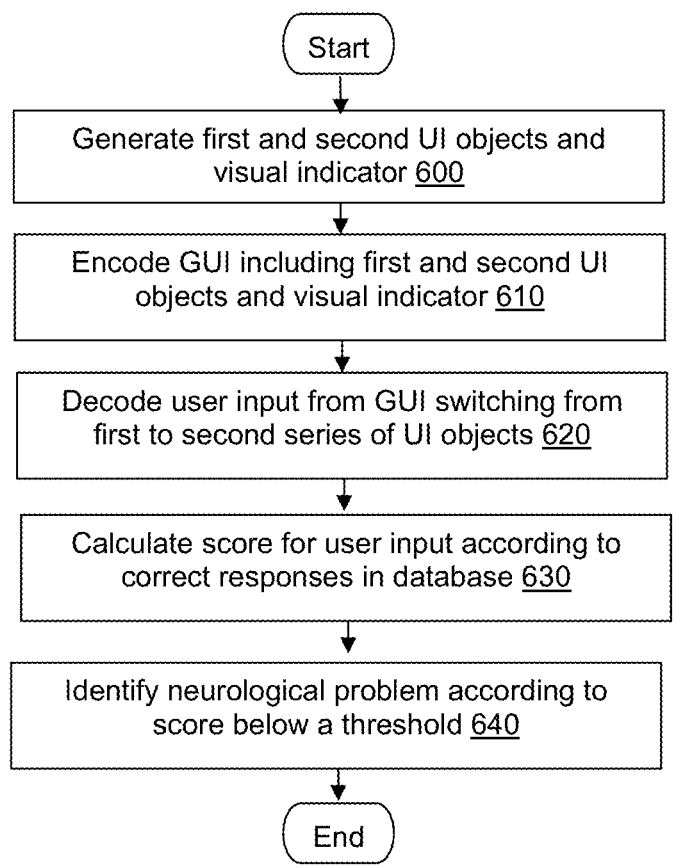
FIG. 6 illustrates a flow diagram for administering and scoring multiple level executive functioning tests and tasks.

FIG. 6 represents a streamlined method of including multiple executive functions within a single task. In step 600, the server generates: a first series of user interface objects comprising a first sequence or a plurality of character string descriptions; a second series of user interface objects comprising a second sequence or a plurality of user interface characteristics; and at least one visual indicator display object requiring a switch between the first series of user interface objects, and the second series of user interface objects. In step 610, the server encodes, for display on a client hardware computing device, a graphical user interface (GUI) comprising the first series of user interface objects, the second series of user interface objects, and the at least one visual indicator display object. In step 620, the server decodes, from the GUI, an electronic input from a user switching from the first series of user interface objects, displayed in association with the visual indicator display object, to the second series of user interface objects. In step 630, the server calculates a score for the electronic input according to the electronic input matching, or failing to match, a correct response associated in a database with a task data defining a function skill demonstrating a cognitive ability of a user. In step 640, responsive to the score being below a predetermined threshold, identify a cognitive decline, a neurological insult, or an early stage disease associated in the database with the score below the predetermined threshold.

Turning now to FIGS. 7-10, the Trail Making subtest may include, as non-limiting examples, Number Sequencing, Letter Sequencing, Complex Switching, Distraction, Working Memory, Visual Scanning, and Motor Speed tasks, each of which is described in detail below. The Trail Making subtest may evaluate executive function domains including Cognitive/Behavioral Control, Cognitive Flexibility (multiple simultaneous tasks), Inhibitory Control, Self-Monitoring, and Rule Violations.

Figure 7:
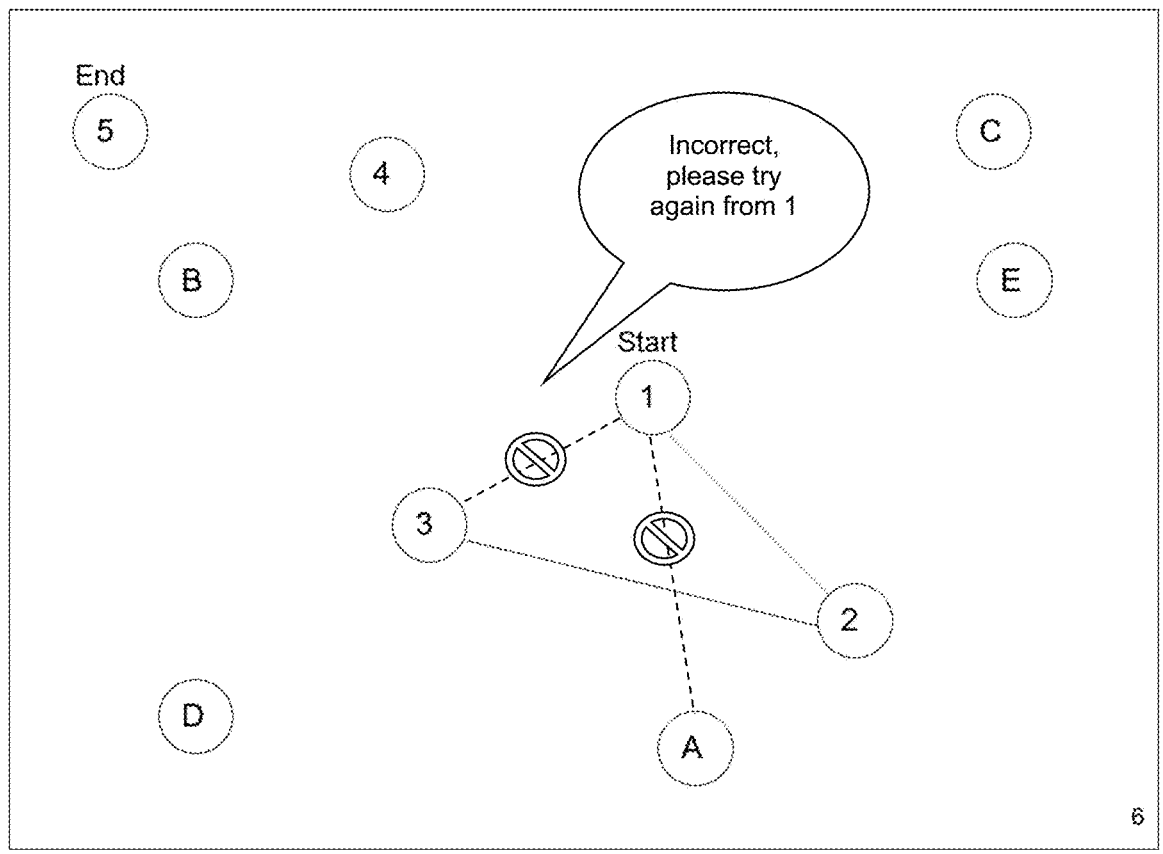
FIG. 7 illustrates an example user interface for administering and scoring multiple level executive functioning tests and tasks.

Turning now to FIG. 7, the examinee GUI for the number sequencing task may display data similar to that in the non-limiting example GUI in FIG. 7, and an examiner GUI may include a client view display, and general and correct/incorrect response instructions, as described above. As seen in FIG. 7, the number sequence examinee GUI may include a combination of circled letters and numbers scattered in random order across the GUI. The instructions may direct the examinee to select the numbers in order and/or to draw a line between the numbers in sequential order, until reaching the end (e.g., the number 5 in FIG. 7).

The examinee may progress through the number sequencing practice test, where correct answers are reinforced and incorrect answers are identified as disclosed above. For example, as seen in FIG. 7, if the examinee selects or proceeds from 1 to 3 (demonstrated by a dotted line), the error feedback may instruct the examinee that the examinee should touch the numbers in order, and thus should have gone from 1 to 2. In this example, the examinee may be instructed to try again starting at 1. In another example seen in FIG. 7, if the examinee selects or proceeds from 1 to A (demonstrated by a dotted line), the error feedback may instruct the examinee that the examinee should touch only the numbers in order, and thus should have gone from 1 to 2. In this example, the examinee may be instructed to try again starting at 1. The examinee may repeat the practice test, and/or take additional practice tests, and after one or more practice tests, the examinee may take the actual test and be scored as described above, according to their selection of the numbers in the correct sequence.

Figure 8:
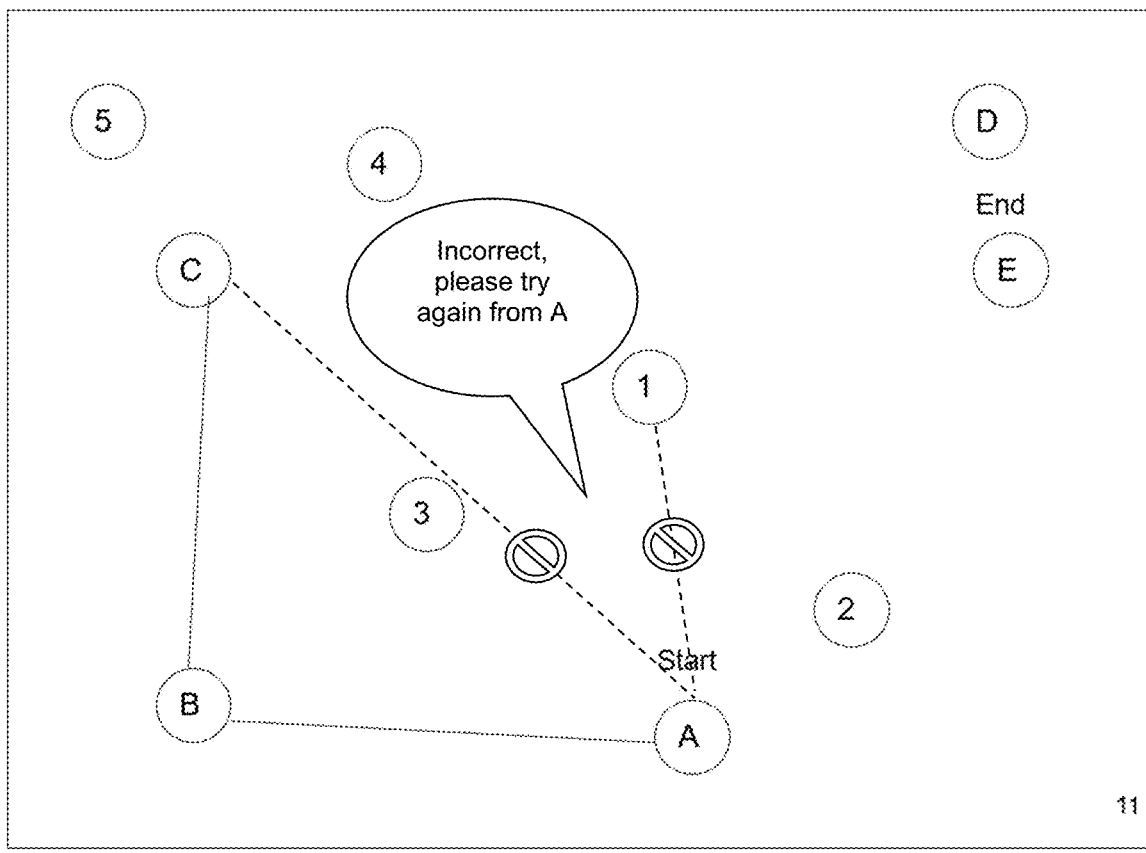
FIG. 8 illustrates an example user interface for administering and scoring multiple level executive functioning tests and tasks.

Turning now to FIG. 8, the examinee GUI for the letter sequencing task may display data similar to that in the non-limiting example GUI in FIG. 8, and an examiner GUI may include a client view display, and general and correct/incorrect response instructions, as described above. As seen in FIG. 8, the letter sequence examinee GUI may include a combination of circled letters and numbers scattered in random order across the GUI. The instructions may direct the examinee to select the letters in order and/or to draw a line between the letters in sequential order, until reaching the end (e.g., the letter E in FIG. 8).

The examinee may progress through the letter sequencing practice test, where correct answers are reinforced and incorrect answers are identified as disclosed above. For example, as seen in FIG. 8, if the examinee selects or proceeds from A to C (demonstrated by a dotted line), the error feedback may instruct the examinee that the examinee should select the letters in order, and thus should have gone from A to B. In this example, the examinee may be instructed to try again starting at A. In another example seen in FIG. 8, if the examinee selects or proceeds from A to 1 (demonstrated by a dotted line), the error feedback may instruct the examinee that the examinee should touch only the letters in order, and thus should have gone from A to B. In this example, the examinee may be instructed to try again starting at A. The examinee may repeat the practice test, and/or take additional practice tests, and after one or more practice tests, the examinee may take the actual test and be scored as described above, according to the selection of the letters in the correct sequence.

Figure 9:
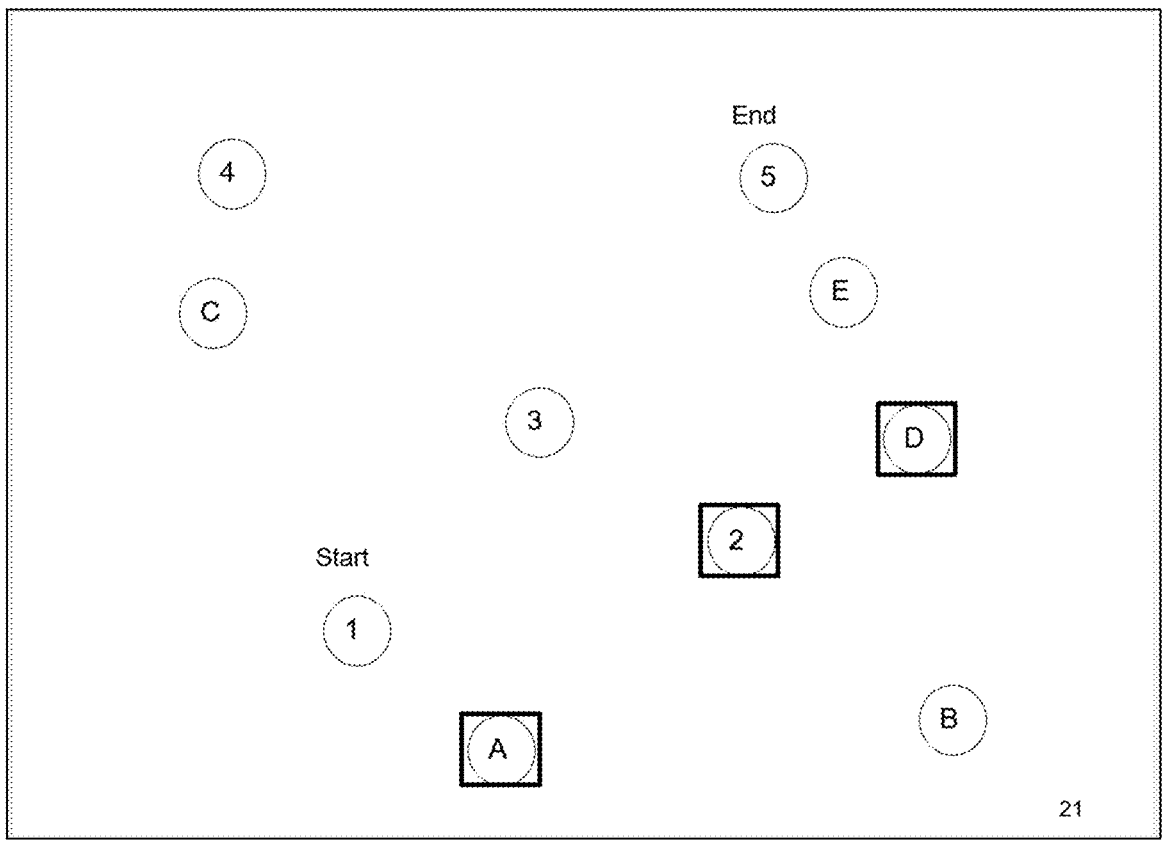
FIG. 9 illustrates an example user interface for administering and scoring multiple level executive functioning tests and tasks.

Though not shown, the examinee GUI for the number/letter switching task may display a combination of circled letters and numbers scattered in random order across the GUI, as seen in FIGS. 7, 8, and 9, and an examiner GUI may include a client view display, and general and correct/incorrect response instructions, as described above. The instruction may direct the examinee to select or draw a line from number 1 to the letter A, then number 2, then the letter B and so on, in order, until reaching the end (e.g., the letter E in FIGS. 7, 8, and 9).

The examinee may progress through the number/letter switching practice test, where correct answers are reinforced and incorrect answers are identified as disclosed above. For example, if the examinee touches or proceeds from 1 to C, the error feedback may instruct the examinee that the examinee switched between numbers and letters, but that they didn't go in order, and thus should have gone from 1 to A. In this example, the examinee should try again starting at 1. In another example, if the examinee touches or proceeds from 1 to 2, the error feedback may instruct the examinee that the examinee needs to remember to switch between numbers and letters in order, and thus should have gone from 1 to A. In this example, the examinee should try again starting at 1. The examinee may repeat the practice test, and/or take additional practice tests, and after one or more practice tests, the examinee may take the actual test and be scored as described above, according to switching between the selection of numbers and letters in the correct sequence.

Turning now to FIG. 9, the examinee GUI for the complex switching task may display data similar to that in the non-limiting example GUI in FIG. 9, and an examiner GUI may include a client view display, and general and correct/incorrect response instructions, as described above. As seen in FIG. 9, the complex switching examinee GUI may include a combination of circled letters and numbers scattered in random order across the GUI, with some of the letters and numbers displayed in boxes. The instructions may be the same as the switching task described above, where the examinee receives instructions to switch between selecting or drawing lines between numbers and letters in order. However, if the number or letter is inside a box, the instructions may direct the examinee not to switch, but select or draw a line from letter to letter or from number to number.

For example, as seen in FIG. 9, the examinee may be instructed to first touch the number 1, and because it is a circle, the examinee should switch and select or draw a line to A. A is in a box, so the instructions may direct the examinee to switch, and select or draw a line to B, which is a circle, so the instructions may direct the examinee to switch and select or draw a line to the next number, 2, and so on, in order, until the examinee reaches the end (e.g., E in FIG. 9).

The examinee may progress through the complex switching practice test, where correct answers are reinforced and incorrect answers are identified as disclosed above. For example, if the examinee touches or proceeds from a number to a letter (or vice versa) when a box is displayed, the error feedback may instruct the examinee that when the number or letter is in a box that the examinee should touch or draw a line to the next number or letter, respectively, in order, and thus should have gone from letter to letter or number to number. In this example, the examinee should try again starting at the last correct letter or number. In another example, if the examinee touches or proceeds from a number to number or letter to letter when a box is not displayed, the error feedback may instruct the examinee that when the number or letter is not in a box that the examinee should switch to select or draw a line to the next letter or number, respectively, in order by switching from number to letter or letter to number according to the last selected number or letter, and thus should have gone from letter to number or number to letter. In this example, the examinee should try again starting at the last correct letter or number. The examinee may repeat the practice test, and/or take additional practice tests, and after one or more practice tests, the examinee may take the actual test and be scored as described above, according to switching, then moving from letter to letter or number to number if the letter or number is within a box.

The GUI and other parameters for the practice test and actual test for the working memory task may have any or all characteristics described above for the number sequencing, letter sequencing, switching, complex switching, or distraction tasks. However, during the practice tests and actual tests, the GUI may display a line between each selected letter and/or number. For example, in the switching task, a line may appear between 1 and A as the user selects or draws a line between each. However, after a limited amount of time, (e.g., one second), the line may then disappear. Thus, the instructions may direct the examinee that the lines will disappear and that the examinee must therefore keep track of their progress through the task.

Though not shown, the examinee GUI for the visual scanning task may display a combination of circled letters and numbers scattered in random order across the GUI, as seen in FIGS. 7, 8, and 9, and an examiner GUI may include a client view display, and general and correct/incorrect response instructions, as described above. However, in the visual scanning task, the GUI may include multiple copies of a single letter (e.g., multiple 3s scattered across the GUI) or number (e.g., multiple Cs scattered across the GUI). The instruction may direct the examinee to select or otherwise mark each of the designated letters or numbers (e.g., draw a line through each of the 3s or Cs).

The examinee may progress through the visual scanning practice test, where correct answers are reinforced and incorrect answers are identified as disclosed above. For example, if the examinee selects numbers other than 3 or C in the example above, the error feedback may instruct the examinee to select only the designated number or letter (e.g. 3s, Cs). In this example, the examinee should try again with the next unmarked 3. The examinee may repeat the practice test, and/or take additional practice tests, and after one or more practice tests, the examinee may take the actual test and be scored as described above, according to correct selection of numbers or letters.

Figure 10:
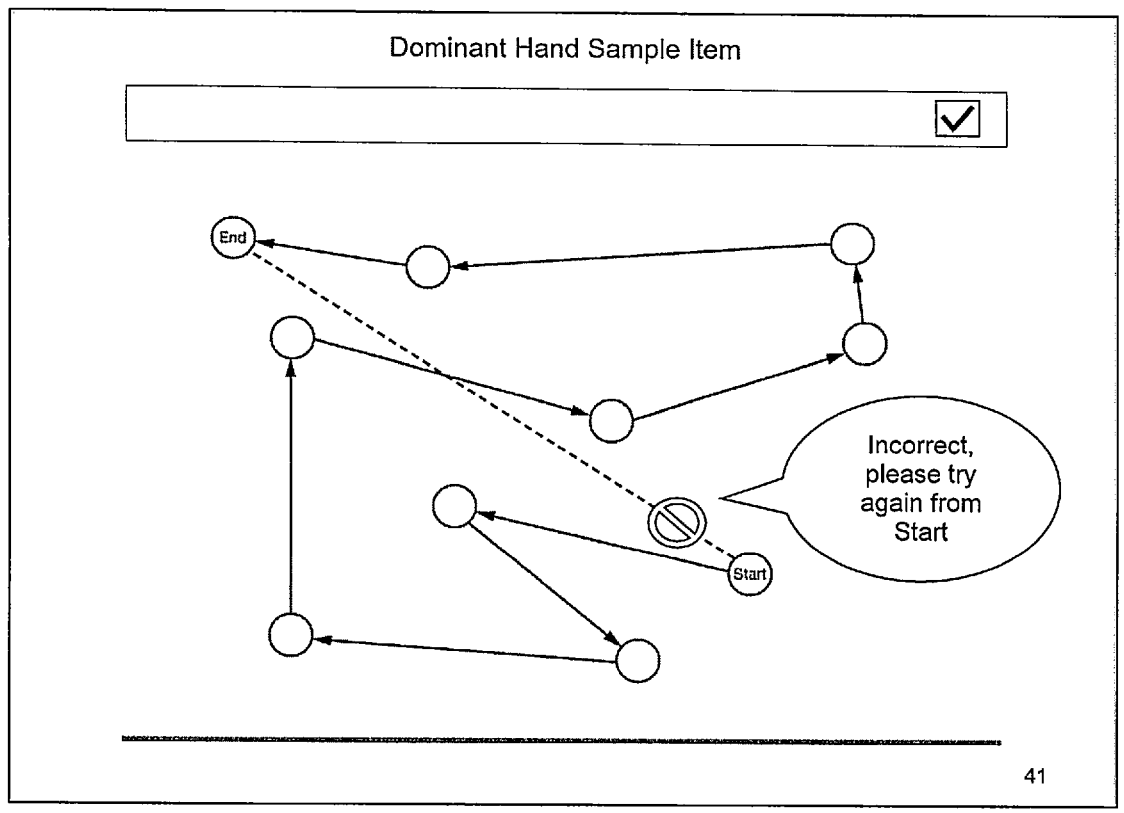
FIG. 10 illustrates an example user interface for administering and scoring multiple level executive functioning tests and tasks.

Turning now to FIG. 10, the examinee GUI for the motor speed task for the examinee's dominant and non-dominant hands may display data similar to that in the non-limiting example GUI in FIG. 10, and an examiner GUI may include a client view display, and general and correct/incorrect response instructions, as described above. As seen in FIG. 10, the motor speed examinee GUI may include a start circle and an end circle, as well as a combination of circles scattered in random order forming a path across the GUI. The instructions may direct the examinee to select the circles and/or to draw a line between circles with a dominant, then a non-dominant hand in sequential order.

The examinee may progress through the motor speed practice tests using their dominant and non-dominant hands, where correct answers are reinforced and incorrect answers are identified as disclosed above. For example, as seen in FIG. 10, if the examinee selects or proceeds through the circles out of order (demonstrated by a dotted line), the error feedback may instruct the examinee to proceed through the circles in order from start to end. In this example, the examinee may be instructed to try again starting at the last correct circle, or at the start circle, as shown. In another example, if the examinee uses the incorrect hand, the error feedback may instruct the examinee to proceed through the circles in order from start to end using the correct hand. In this example, the examinee may try again using the correct hand. The examinee may repeat the practice test, and/or take additional practice tests, and after one or more practice tests, the examinee may take the actual test using both dominant and non-dominant hands, and be scored as described above, according to their selection of the circles in the correct sequence.

The GUI and other parameters for the practice test and actual test for the switching with distraction task may have any or all characteristics described above for any of the previously disclosed trail making tasks. However, during the practice tests and actual tests, the examinee may hear sounds and see objects on the screen. The instructions may direct the examinee to ignore the sounds or displayed objects, and focus only on selecting, drawing lines, and/or switching between the numbers and letters in the correct order.

Figure 18:
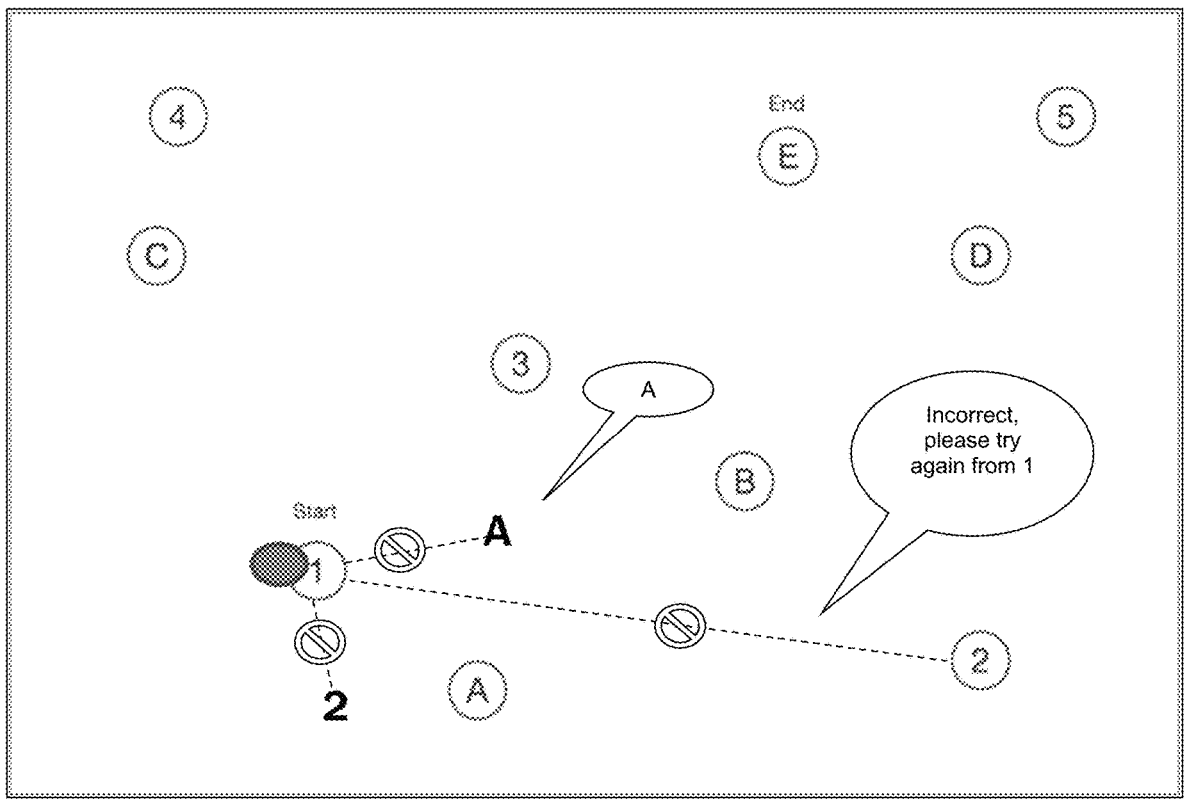
FIG. 18 illustrates an example user interface for administering and scoring multiple level executive functioning tests and tasks.

Turning now to FIG. 18, the examinee GUI for the number/letter switching task with distractions (possibly including auditory distractions) may display data similar to that in the non-limiting example GUI in FIG. 18, and an examiner GUI may include a client view display, and general and correct/incorrect response instructions, as described above. As seen in FIG. 18, the switching with distraction examinee GUI may include a combination of circled letters and numbers scattered in random order across the GUI. The instructions may be the same as the number/letter switching task described above, where the examinee receives instructions to switch between selecting or drawing lines between numbers and letters in order.

The switching with distraction GUI, as part of the trail making test, may also include an additional condition, including visual or audio distractions, possibly stored within, and generated by, the disclosed system, which continue throughout the task. The more general tests may therefore be administered first, and then again with the distractions tasks added to the assessment. The distraction task may introduce competing stimuli to the original task to distract an examinee from accurately completing the task. By using the same scoring rubric the differences may be analyzed.

Given the computer-based nature of the disclosed embodiments, the system may generate visual or audio stimuli, from visual and audio files stored on within the system, which is presented at particular times during the task to distract the user from the task objective. Thus, in some embodiments, these distractions may include an audio file including a voice saying numbers and letters. In some embodiments, numbers and letters may be generated in such a way that they appear and disappear from the switching with distraction examinee GUI. However, unlike the combination of numbers and letters spread across the screen, as disclosed above, the generated letters and number may be displayed without a circle, as seen for the letter A and the number 2 in FIG. 18.

In embodiments such as the example embodiment in FIG. 18, the examinee may be instructed that they may hear a voice say numbers and letters and/or see numbers and letters, which will not be in circles and will appear and disappear on the screen. For example, the examinee may be instructed to first touch the number 1, but never to touch a distraction number or letter (e.g., the 2 or A that are displayed in FIG. 18), then to switch and select or draw a line to A within a circle. The instructions may further direct the examinee to continue switching, for example, proceeding from A to 2, and from 2, selecting or draw a line to B, and so forth, so that the instructions may direct the examinee to switch and select or draw lines switching between numbers and letters within circles, in order, until the examinee reaches the end (e.g., E in FIG. 18).

As the examinee progresses through the switching task with distractions, the system may access and play the audio files, possibly including a voice saying numbers or letters as contained in the audio file, and/or access and display any combinations of letters and numbers without a circle (e.g., "A" in FIG. 18), scattered across the GUI in random order, but in different positions than the numbers and letters including the circle. Thus, the audio files and/or the letters and numbers without circles may act as distractors to the examinee, so that while the examinee is conducting the tasks, non-random misleading audio and visual distractions may be introduced.

In some embodiments the placement of the combination of letters or numbers may be designed to appear in orders or positions calculated to make the user want to click on the distraction. For example, the distractors may be time-linked to the behavior of the examinee based on the next expected response by the system in such a way as to push the examinee towards an incorrect response, which the user will need to ignore to correctly complete the task.

One or more algorithms within the disclosed system may determine the type of potential distractor, and when to display the potential distractors. In some embodiments, the locations of the distractors may be preprogrammed locations according to the visual or other proximity to the current number/letter within a circle in the trail making task. In some embodiments, the user may also be required to avoid connecting lines where the lines stay present.

As a non-limiting example, in FIG. 18, the user may be instructed to begin the practice or actual testing by selecting the circled number 1. The examinee GUI may further include a display of a non-circle number 1, along with other potential distractors. The user may then be instructed to proceed, and may proceed, from 1 to A, from A to 2, from 2 to B, and so on. As seen in FIG. 18, the examinee may touch or click the 1 within the circle, as instructed (indicated by the filled oval in FIG. 18), and the system may remove the display of the non-circle 1, and select and present, for display on the examinee GUI, additional distractors, such as the non-circle letter A (possibly including the accompanying audio file) and the number 2. In this example embodiment, the non-circle 1, 2, and A may all be displayed in the same font type and size as the numbers and letters inside circles.

Though not shown, once the user selects A (or draws a line from 1 to A), the non-circle B may appear, the non-circle 2 may stay, and, in embodiments including an audio component, the audio file may include a voice saying "B," and so forth.

As seen in FIG. 18 and noted above, the layouts for the trail making tasks may be designed so that the distractors have a visual proximity to similar or current numbers or letters within circles along the path, in an attempt to trick the user or pull them away from the correct sequence within the path. The visual distractors may also be accompanied by audio distractors, both of which may be selected as audio files and visual files by the system and presented at the same time. The numbers or letters within circles, and the non-circle distractor numbers or letters may therefore be related but incongruous.

The progression described thus far may continue throughout the practice or actual tests, removing some letters or numbers and replacing them with others displayed on the switching and distraction GUI.

The examinee may progress through the number/letter switching practice test with distractions, where correct answers are reinforced and incorrect answers are identified as disclosed above. For example, if the examinee touches or proceeds from 1 to C, the error feedback may instruct the examinee that the examinee switched between numbers and letters, but that they didn't go in order, and thus should have gone from 1 to A. In this example, the examinee should try again starting at 1. In another example, if the examinee touches or proceeds from 1 to 2, the error feedback may instruct the examinee that the examinee needs to remember to switch between numbers and letters in order, and thus should have gone from 1 to A. In this example, the examinee should try again starting at 1.

The examinee may repeat the practice test, and/or take additional practice tests, and after one or more practice tests, the examinee may take the actual test and be scored as described above, according to switching between the selection of numbers and letters in the correct sequence.

The scoring rubric may directly compare the performance of the practice or actual test with distractions to an identical task without the distractions, in order to determine what the cost of distraction for that examinee. The system may therefore anticipate examinees taking the practice or actual test with and without the distractors in order to generate a delta to determine the effect of distractors on the people.

The scoring rubric for the number and letter switching task with distractors may be incorporated into the scoring rubric generally. As noted above, the distractors may affect the time required to complete the tasks within the instructions, which may, in turn, create a more focused identification of the reason for the cognitive decline following head trauma or neurological insult, for example. Thus, a primary variable for scoring each of the tasks is the speed it takes an examinee to complete it. If this time increases significantly in the presence of a distraction, the examinee's likelihood that the user is easily distracted is also increased.

The disclosed embodiments may also assess examinees who perform the test well when there are no distractions, and compare this with distraction embodiments, do determine whether the examinees make errors when there are distractions. In other words, in distraction embodiments, the distractions may both slow down the user, and may cause them to make the wrong choice. For example, the user may make sequencing or switching errors as disclosed above, and the scoring rubric may be adjusted to consider error rate and types of errors in scoring the examinee.

Additional responsive embodiments may be envisioned, wherein, as the user performs better and better, additional increased difficulty for distractions are introduced. For example, the user may begin with only audio distractions, and as they continue to progress, visual distractions may be introduced, or vice versa. In some embodiments, the types of distractors may be particularly distracting to a particular type of person (e.g., person distracted by visual more than audio distractors, for example).

Thus, the Trail Making subtest may evaluate executive function domains including Cognitive/Behavioral Control, Inhibitory Control, Self-Monitoring, and Rule Violations to determine the cognitive abilities of the examinee. Specifically, the number sequencing, letter sequencing, and motor speed tasks track the examinee's cognitive abilities to select or connect dots in consecutive order. The visual scanning task likewise tracks the examinee's cognitive ability to recognize instances of the same letter or number within the GUI field.

The Trail Making subtest also demonstrates the Cognitive Flexibility executive function domain. The input task data demonstrates multiple simultaneous function skills to determine the cognitive abilities of the examinee being used simultaneously. Specifically, the distraction task tests the examinee's cognitive ability to ignore distractions while maintaining the ability to proceed sequentially through any of the disclosed tests. The switching task tracks the examinee's cognitive ability to switch while maintaining the ability to proceed sequentially through the disclosed tests. The complex switching task tracks the examinee's cognitive ability to switch or continue with the same sequence in switching tasks, by proceeding letter to letter or number to number if a visual cue is provided. The working memory task tracks the examinee's cognitive ability to proceed through any combination of the disclosed tests without visual cues for the examinee's previous progress.

Though not shown, the Verbal Fluency subtest may include, as non-limiting examples, Letter Fluency, Category Fluency, and Switching tasks, each of which is described in detail below. The Verbal Fluency subtest may evaluate executive function domains including Cognitive/Behavioral Control, Cognitive Flexibility (multiple simultaneous tasks), Rule Violations, and Behavioral Productivity (Initiation).

Though not shown, the examinee GUI for the letter fluency task may provide a letter, either as an audio file, or displayed on the letter fluency examinee GUI, and a GUI control (e.g., text box, text area, audio capture, etc.), for receiving input from the user. An examiner GUI may include a client view display, and general and correct/incorrect response instructions, as described above. The instructions may direct the examinee to enter or speak as many words that start with the provided letter that the examinee can think of during the provided time period (e.g., 60 seconds).

The examinee may progress through the letter fluency practice test, where correct answers are reinforced and incorrect answers are identified as disclosed above. For example, if the examinee is given the letter F, and enters one or more entries that do not begin with the letter F, the error feedback may instruct the examinee to enter words beginning with the letter F. In this example, the examinee may try again starting at the incorrect entry. The examinee may repeat the practice test, and/or take additional practice tests, and after one or more practice tests, the examinee may take the actual test and be scored as described above, according to their ability to list words starting with the correct letter.

Though not shown, the examinee GUI for the category fluency task may provide a category (e.g., animals, fruits and vegetables, instruments, clothing, etc.), either as an audio file or displayed on the category fluency examinee GUI, and a GUI control for receiving input from the user as described above. An examiner GUI may include a client view display, and general and correct/incorrect response instructions, as described above. The instructions may direct the examinee to enter or speak as many words that belong to the provided category that the examinee can think of during the provided time period.

The examinee may progress through the category fluency practice test, where correct answers are reinforced and incorrect answers are identified as disclosed above. For example, if the examinee is given the category animals, and enters one or more entries that do not belong to that category, the error feedback may instruct the examinee to enter words that belong to the correct category (animals). In this example, the examinee may try again starting at the incorrect entry. The examinee may repeat the practice test, and/or take additional practice tests, and after one or more practice tests, the examinee may take the actual test and be scored as described above, according to their ability to list words associated with the correct category.

Though not shown, the examinee GUI for the letter/category fluency task may provide a letter and a category, either as audio files or displayed on the letter/category fluency examinee GUI, and a GUI control for receiving input from the user as described above. An examiner GUI may include a client view display, and general and correct/incorrect response instructions, as described above. The instructions may direct the examinee to enter or speak as many words that both include the provided letter, and also belong to the provided category, that the examinee can think of during the provided time period.

The examinee may progress through the letter/category fluency practice test, where correct answers are reinforced and incorrect answers are identified as disclosed above. For example, if the examinee is given the letter F and the category animals, and enters one or more entries that do not contain the letter and/or do not belong to that category, the error feedback may instruct the examinee to enter words that include the letter and belong to the correct category. In this example, the examinee may try again starting at the incorrect entry. The examinee may repeat the practice test, and/or take additional practice tests, and after one or more practice tests, the examinee may take the actual test and be scored as described above, according to their ability to list words including the correct letter and associated with the correct category.

The GUI and other parameters for the practice test and actual test for the category/letter switching task may have any or all characteristics described above for the letter, category, and/or letter/category fluency tasks. However, during the practice tests and actual tests, the instructions may direct the examinee to alternate between listing words starting with the provided letter and listing words belonging to the provided category.

Thus, the Verbal Fluency subtest may evaluate executive function domains including Cognitive/Behavioral Control; Rule Violations; and Behavioral Productivity (Initiation) to determine the cognitive abilities of the examinee. Specifically, the letter fluency, category fluency, and letter/category fluency tasks track the examinee's cognitive abilities to list words associated with the letter and/or category. The Verbal Fluency subtest also demonstrates the Cognitive Flexibility executive function domain. The input task data demonstrates multiple simultaneous function skills to determine the cognitive abilities of the examinee being used simultaneously. Specifically, the letter/category fluency task tests the examinee's cognitive ability to list words including both the letter and category provided. The category/letter switching task tracks the examinee's cognitive ability to switch while maintaining the ability to provide words alternating between letter and category.

Turning now to FIG. 11, the Design Fluency subtest may include, as non-limiting examples, Mixed Dots, Switching, and Distraction tasks, each of which is described in detail below. The Design Fluency subtest may evaluate executive function domains including Cognitive/Behavioral Control, Cognitive Flexibility (multiple simultaneous tasks), Self-Monitoring, Rule Violations, and Behavioral Productivity (Initiation).

As seen in FIG. 11, the examinee GUI for the mixed dots task may display data similar to that in the client view of the non-limiting example GUI in FIG. 11, and an examiner GUI may include a client view display, and general and correct/incorrect response instructions similar to those shown in FIG. 11, and as described above. As seen in the client view of FIG. 11, the mixed dots examinee GUI may include any combination of filled dots and empty dots scattered in random order across the GUI. The instructions (which differ from those displayed in FIG. 11) may direct the examinee to draw 4 lines connecting any combination of filled or empty dots in order to design a unique pattern with lines and dots. The examinee may further be instructed to click a "next" button in order to create multiple patterns, each of which should be unique and distinct from any previous patterns.

The examinee may progress through the mixed dots practice test, where correct answers are reinforced and incorrect answers are identified as disclosed above. For example, if the examinee creates a pattern using more or less than 4 lines between dots, the error feedback may instruct the examinee that the examinee should use no more or less than 4 lines created by connecting dots and thus should have connected at least 4 sets of dots to create the unique pattern. In this example, the examinee may try again either to redesign an existing design, or by starting a new design. In another example, if the examinee creates two identical designs, the error feedback may instruct the examinee that two or more of the designs are the same, and that each design created by the examinee should be unique and distinct from any previously created designs. In this example, the examinee should try again either to redesign an existing design, or by starting a new design. The examinee may repeat the practice test, and/or take additional practice tests, and after one or more practice tests, the examinee may take the actual test and be scored as described above, according to their design of unique designs using 4 lines between the provided dots.

The GUI and other parameters for the practice test and actual test for the filled/empty dot switching task may have any or all characteristics described above for the mixed dots task. However, in addition to directing the examinee to create 4 distinct designs using 4 lines between dots, the instructions may further direct the examinee to switch between touching and/or drawing lines between filled dots and empty dots, as seen in the client view of FIG. 11.

The examinee may progress through the filled/empty dot switching practice test, where correct answers are reinforced and incorrect answers are identified as disclosed above. For example, in addition to the error feedback provided in the mixed dots examples above, if the examinee creates a pattern, but does not create the pattern by alternating between empty dots and filled dots, the error feedback may instruct the examinee that the examinee should remember to make each line by switching between empty and filled dots. In this example, the examinee should try again starting at the last correct line alternating between empty and filled dots, or possibly creating a new pattern. The examinee may repeat the practice test, and/or take additional practice tests, and after one or more practice tests, the examinee may take the actual test and be scored as described above, according to their design of unique designs using 4 lines alternating between the provided empty and filled dots.

The GUI and other parameters for the practice test and actual test for the design with distraction task may have any or all characteristics for the mixed dots task and/or the empty/filled dot switching task described above. However, during the practice tests and actual tests, the examinee may hear sounds and see objects on the screen. The instructions may direct the examinee to ignore the sounds or displayed objects, and focus only on designing the designs according to the instructions.

Thus, the Design Fluency subtest may evaluate executive function domains including Cognitive/Behavioral Control, Self-Monitoring, Rule Violations, and Behavioral Productivity (Initiation) to determine the cognitive abilities of the examinee. Specifically, the mixed dots task tracks the examinee's cognitive abilities to design multiple unique designs using 4 lines between the provided dots. The Design Fluency subtest also demonstrates the Cognitive Flexibility executive function domain. The input task data demonstrates multiple simultaneous function skills to determine the cognitive abilities of the examinee being used simultaneously. Specifically, the filled/empty dot switching task tests the examinee's cognitive ability to design unique designs using 4 lines between dots while simultaneously alternating between the provided empty and filled dots. The design with distraction task tests the examinee's cognitive ability to ignore distractions while maintaining the ability to design unique designs in combination with any of the disclosed tests.

Turning now to FIG. 12, the Color Word Interference subtest may include, as non-limiting examples, Color Identification, Word Identification, Inhibition, Switching, and Distraction tasks, each of which is described in detail below. The Color Word Interference subtest may evaluate executive function domains including Cognitive/Behavioral Control, Cognitive Flexibility (multiple simultaneous tasks), Inhibitory Control, Self-Monitoring, and Rule Violations.

Returning now to FIG. 12, the examinee GUI for the color identification task may display data similar to that in the client view of the non-limiting example GUI in FIG. 12, and an examiner GUI may include a client view display, and general and correct/incorrect response instructions, similar to those seen in FIG. 12, and as described above. As seen in FIG. 12, the color identification examinee GUI may include a series of boxes, including a box in a first top row, and multiple boxes in a lower row. Though not shown in FIG. 12, the examinee GUI for the color identification task may fill the top row box with a solid color. The multiple boxes in the lower row may each display a text string forming a word describing a color. The instructions (which differ from those displayed in FIG. 12) may direct the examinee to select the word in one of the multiple boxes in the lower row that describes the solid color in the top row box.

The examinee may progress through the color identification practice test, where correct answers are reinforced and incorrect answers are identified as disclosed above. For example, if the top row box displays a red filled box, and the examinee selects a box containing a word describing a color other than that in box in the first top row (e.g., blue), the error feedback may instruct the examinee that the examinee should select the box including the word for the color (e.g., red), and thus should have selected the box with the text string red rather than blue. In this example, the examinee may try again starting with a new top row box and new boxes on the lower row, or restart the previous task. The examinee may repeat the practice test, and/or take additional practice tests, and after one or more practice tests, the examinee may take the actual test and be scored as described above, according to their selection of the correct box containing the word describing the displayed color.

Returning to FIG. 12, the examinee GUI for the word identification task may display data similar to that in the client view of the non-limiting example GUI in FIG. 12, and an examiner GUI may include a client view display, and general and correct/incorrect response instructions, similar to those seen in FIG. 12, and as described above. As seen in FIG. 12, the word identification examinee GUI may include the rows and boxes described above. As seen in FIG. 12, the examinee GUI for the top row box of the word identification task may include a text string forming a word describing a color. The multiple boxes in the lower row may each also display a text string forming a word describing a color, and one of these boxes may match the text string in the box in the first top row. The instructions (which differ from those displayed in FIG. 12) may direct the examinee to select the word in one of the multiple boxes in the lower row that matches the text string forming the word in the box in the top row.

The examinee may progress through the word identification practice test, where correct answers are reinforced and incorrect answers are identified as disclosed above. For example, if the box in the first top row displays the word "blue", and the examinee selects a box containing a word describing a color other than that in box in the first top row (e.g., red), the error feedback may instruct the examinee that the examinee should select the box including the word matching the box in the first top row (e.g., blue or green), and thus should have selected the box with blue rather than red. In this example, the examinee may try again starting with a new top row box and new boxes on the lower row, or restart the previous task. The examinee may repeat the practice test, and/or take additional practice tests, and after one or more practice tests, the examinee may take the actual test and be scored as described above, according to their selection of the correct box containing the word matching the word in the first top row box.

Returning to FIG. 12, the examinee GUI for the color word inhibition task may display data similar to that in the client view of the non-limiting example GUI in FIG. 12, and an examiner GUI may include a client view display, and general and correct/incorrect response instructions, similar to those seen in FIG. 12, and as described above. As seen in FIG. 12, the word identification examinee GUI may include the rows and boxes described above. However, in FIG. 12, the examinee GUI for the top row box of the word identification task may include a text string forming a word describing a color, but may be displayed in a font color other than the color described by the text string. The multiple boxes in the lower row may each display a text string forming a word describing a color, and one of these boxes may match a text string forming a word describing the font color of the text string within the top row box. The instructions may direct the examinee to select the word in one of the multiple boxes in the lower row that matches the font color of the text string forming the word within the top row box.

The examinee may progress through the color word inhibition practice test, where correct answers are reinforced and incorrect answers are identified as disclosed above. For example, if the top row box displays the word "blue," but is displayed in a red font, and the examinee selects a box containing a word describing a color other than the font color for the word within the top row box (e.g., blue, as shown in FIG. 12, or green), the error feedback may instruct the examinee that the examinee should select the box including the word matching the font color of the word within the top row box (e.g., red), and thus should have selected the box with red rather than blue or green. In this example, the examinee may try again starting with a new top row box and new boxes on the lower row, or restart the previous task. The examinee may repeat the practice test, and/or take additional practice tests, and after one or more practice tests, the examinee may take the actual test and be scored as described above, according to their selection of the correct box containing the word matching the font color of the word in the first top row box.

The GUI and other parameters for the practice test and actual test for the color/word switching task may have any or all characteristics described above for the color identification, the word identification, and/or the color word inhibition tasks described above. However, in addition to directing the examinee to select the correct color or word in the top row box, the instructions may further direct the examinee that if the top row box includes a visual indicator (e.g., the outline or background for the box is yellow), to select either a box in the lower row that matches the word in the top row box, or to select the box in the lower row containing the word that matches the color or font color of the word in the top row box, thereby switching between identifying words and identifying colors according to the instructions, as seen in FIG. 12.

The examinee may progress through the color/word switching practice test, where correct answers are reinforced and incorrect answers are identified as disclosed above. For example, in addition to the error feedback provided in the color identification, word identification, and/or color/word task inhibition examples above, if the examinee selects a word matching the word in the top row box, because of the yellow outline around, or background within, the box, when they should have selected the word describing the color, or vice versa, according to the instructions, the error feedback may instruct the examinee that the examinee should switch when the yellow outline is around the box, according to the instructions. In this example, the examinee should try again starting at the last correct color or word match selection, or possibly creating a new examinee GUI. The examinee may repeat the practice test, and/or take additional practice tests, and after one or more practice tests, the examinee may take the actual test and be scored as described above, according to their selection of correct matches to colors and words, based on the visual indicator and the instructions.

The GUI and other parameters for the practice test and actual test for the color word interference with distraction task may have any or all characteristics for color identification, word identification, inhibition, and/or switching tasks described above. However, during the practice tests and actual tests, the examinee may hear sounds and see objects on the screen. The instructions may direct the examinee to ignore the sounds or displayed objects, and focus only on selecting the correct colors or words in the boxes according to the instructions.

Figure 19:
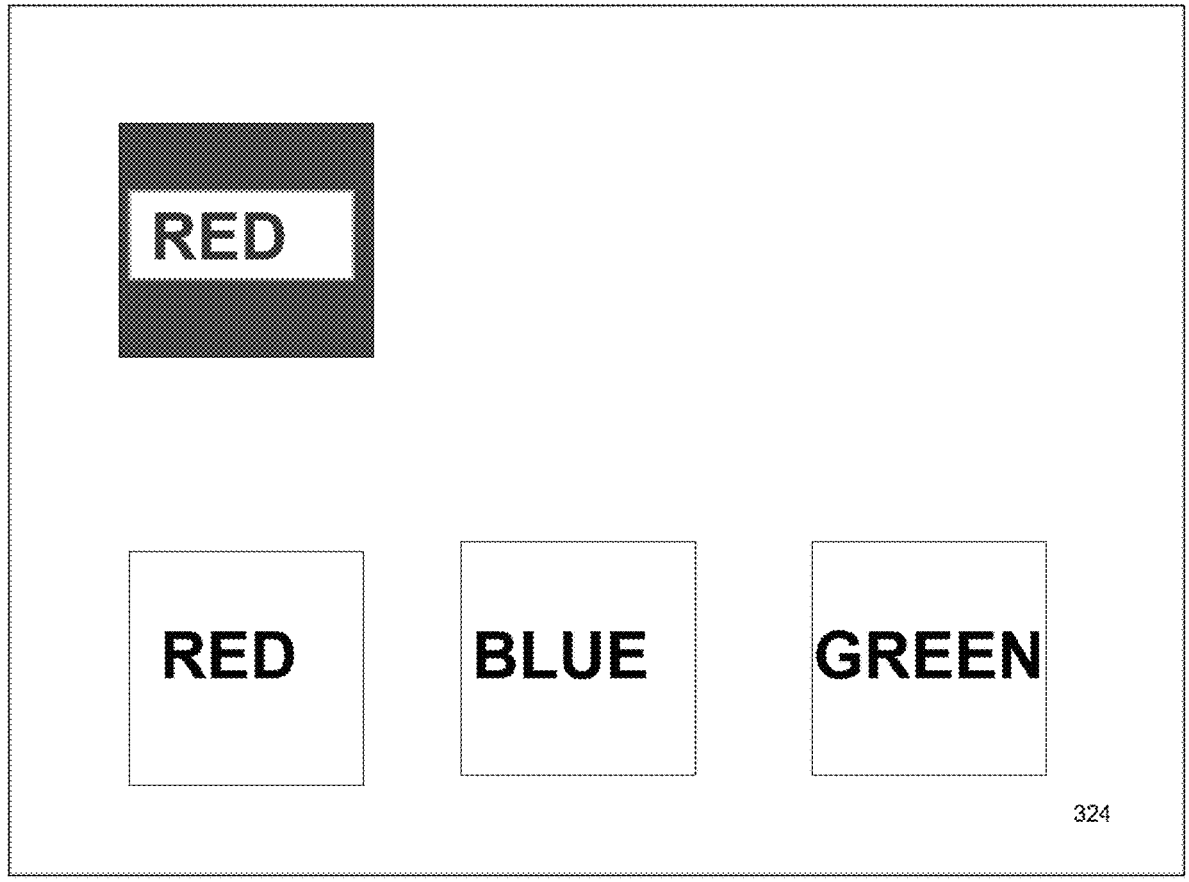
FIG. 19 illustrates an example user interface for administering and scoring multiple level executive functioning tests and tasks.

Turning now to FIG. 19, the examinee GUI for the color word inhibition task may display data similar to that in the client view of the non-limiting example GUI in FIG. 19, and an examiner GUI may include a client view display, and general and correct/incorrect response instructions, similar to those seen in FIG. 19, and as described above. As seen in FIG. 19, the word identification examinee GUI may include the rows and boxes described above.

However, in FIG. 19, the examinee GUI for the top row box of the word identification task may not only include a text string forming a word describing a color, but may also: be displayed within a font color the same as, or other than, the color described by the text string, as described above; include a filled box, as described above; include a visual indicator (e.g., the outline or background for the box is yellow), possibly to indicate a switching task, as described above; include a filled box, with a color other than the text string forming the word, or the color described by the text string, as described above; and/or be offset from the center to the left or the right, or possibly including offsets within the box itself to the left or right, as seen in FIG. 19.

The multiple boxes in the lower row may each display a text string forming a word describing a color, and one of these boxes may match a text string forming a word describing the font color of the text string within the top row box. In some embodiments, the multiple boxes in the lower row may display text describing colors of additional elements, such as the color of the box, the color of the outline or background, the color filling the box, etc. The instructions may direct the examinee to select the word in one of the multiple boxes in the lower row that matches the font color of the text string forming the word (or other colors) within the top row box.

The additional colors, as well as the left and right offsets within the top row box, may act as distractors within the practice or actual tests. For example, FIG. 19 includes the top row box of the color word inhibition task, which is offset to the left of the screen (i.e., not centered within the GUI or relative to the multiple boxes in the lower row). The top row box is also offset to the left, and includes the text string "RED." As a non-limiting example, the text "RED" may be displayed in a blue font color, within a box filled with red, possibly with a highlighted outline, etc. The multiple boxes in the lower row may include a description of any of these colors and, according to the instructions, the user may be instructed to select the matching text, or any of the matching colors in the top row box.

These distractions are unique from the trail making test and other distractions discussed above. They takes advantage of the human tendency and inability to stop engaging in an overlearned behavior, despite instruction to the contrary. For example, a user that sees the word RED automatically thinks red, even if the instructions have the user focus on the color blue (e.g., the background of the box, the font color of the word RED, etc., directing the user to focus on the actual word, or the color of the word or background color, etc. according to whether the box includes an outline (e.g., yellow outline)).

As noted above, an additional distraction may include movement of the box around the screen. In some embodiments, rather than providing a response stimuli that always appears in the center of the GUI, where the user's attention and focus are naturally focused, some embodiments may move the top row box to the left or the right, requiring the user to track the information in the box, thereby adding an additional level of attentional regulation required by the user. This distraction also takes advantage of the Simon effect, wherein people tend to respond to stimuli that appear within the same visual field or area. For example, if the stimulus appears in the left side of the GUI, the user will be more naturally pulled to want to touch the response that's on the left side of the GUI rather than the correct answer, which may be in the center or on the right side of the GUI. By moving the visual stimuli, the user must inhibit the tendency to stay on the same side of the GUI.

This positional distractor may therefore provide an additional layer of distraction, regulating two different types of inhibitory control, so that in FIG. 19, for example, if the instructions were for the user to select the font color of the top row box (blue), the user would have a tendency to select the box containing RED, since it has a common word, and is on the left side of the GUI, where the user's attention is naturally focused. In addition, the background of each box may add another layer of distraction.

The examinee may progress through the color word inhibition practice test, where correct answers are reinforced and incorrect answers are identified as disclosed above. For example, if the instructions require the user to select the lower row box matching the font color, and the top row box displays the word "red," but is displayed in a blue font, and the examinee selects a box containing a word describing a color other than the font color for the word within the top row box (e.g., red, as shown in FIG. 19, or green), the error feedback may instruct the examinee that the examinee should select the box including the word matching the font color of the word within the top row box (e.g., blue), and thus should have selected the box with blue rather than red or green. In this example, the examinee may try again starting with a new top row box and new boxes on the lower row, or restart the previous task.

The GUI and other parameters for the practice test and actual test for the color word interference with distraction task may have any or all characteristics for color identification, word identification, inhibition, and/or switching tasks described above. However, during the practice tests and actual tests, the examinee may be presented with any of the distractors described above. The instructions may direct the examinee to ignore these distractors, and focus only on selecting the correct colors or words in the boxes according to the instructions.

The examinee may repeat the practice test, and/or take additional practice tests, and after one or more practice tests, the examinee may take the actual test and be scored as described above, according to their selection of the correct box containing the word matching the font color of the word in the first top row box.

The scoring rubric may directly compare the performance of the practice or actual test with distractions to an identical task without the distractions, in order to determine what the cost of distraction for that examinee. The system may therefore anticipate examinees taking the practice or actual test with and without the distractors in order to generate a delta to determine the effect of distractors on the people.

The scoring rubric for the color word inhibition task with distractors may be incorporated into the scoring rubric generally. As noted above, the distractors may affect the time required to complete the tasks within the instructions, which may, in turn, create a more focused identification of the reason for the cognitive decline following head trauma or neurological insult, for example. Thus, a primary variable for scoring each of the tasks is the speed it takes an examinee to complete it. If this time increases significantly in the presence of a distraction, the examinee's likelihood that the user is easily distracted is also increased.

The disclosed embodiments may also assess examinees who perform the test well when there are no distractions, and compare this with distraction embodiments, do determine whether the examinees make errors when there are distractions. In other words, in distraction embodiments, the distractions may both slow down the user, and may cause them to make the wrong choice. For example, the user may make sequencing or switching errors as disclosed above, and the scoring rubric may be adjusted to consider error rate and types of errors in scoring the examinee.

Additional responsive embodiments may be envisioned, wherein, as the user performs better and better, additional increased difficulty for distractions are introduced. For example, the user may begin with only audio distractions, and as they continue to progress, visual distractions may be introduced, or vice versa. In some embodiments, the types of distractors may be particularly distracting to a particular type of person (e.g., person distracted by visual more than audio distractors, for example).

Thus, the Color Word Interference subtest may evaluate executive function domains including Cognitive/Behavioral Control, Inhibitory Control, Self-Monitoring, and Rule Violations tests to determine the cognitive abilities of the examinee. Specifically, the color identification, word identification, and color word inhibition tasks track the examinee's cognitive abilities to select the correct word matching the color, word, and/or font color of the top row box.

The Color Word Interference subtest also demonstrates the Cognitive Flexibility executive function domain. The input task data demonstrates multiple simultaneous function skills to determine the cognitive abilities of the examinee being used simultaneously. Specifically, the color word inhibition task tests the examinee's cognitive ability to select the font color of the word in the top row box, rather than the word itself. The switching task tracks the examinee's cognitive ability to switch while maintaining the ability to select the correct color or word according to the visual indicator (e.g., yellow outline or background). The color/word identification and/or switching task with distraction tests the examinee's cognitive ability to ignore distractions while maintaining the ability to select the correct word or color in combination with any of the disclosed tests.

Figure 13:
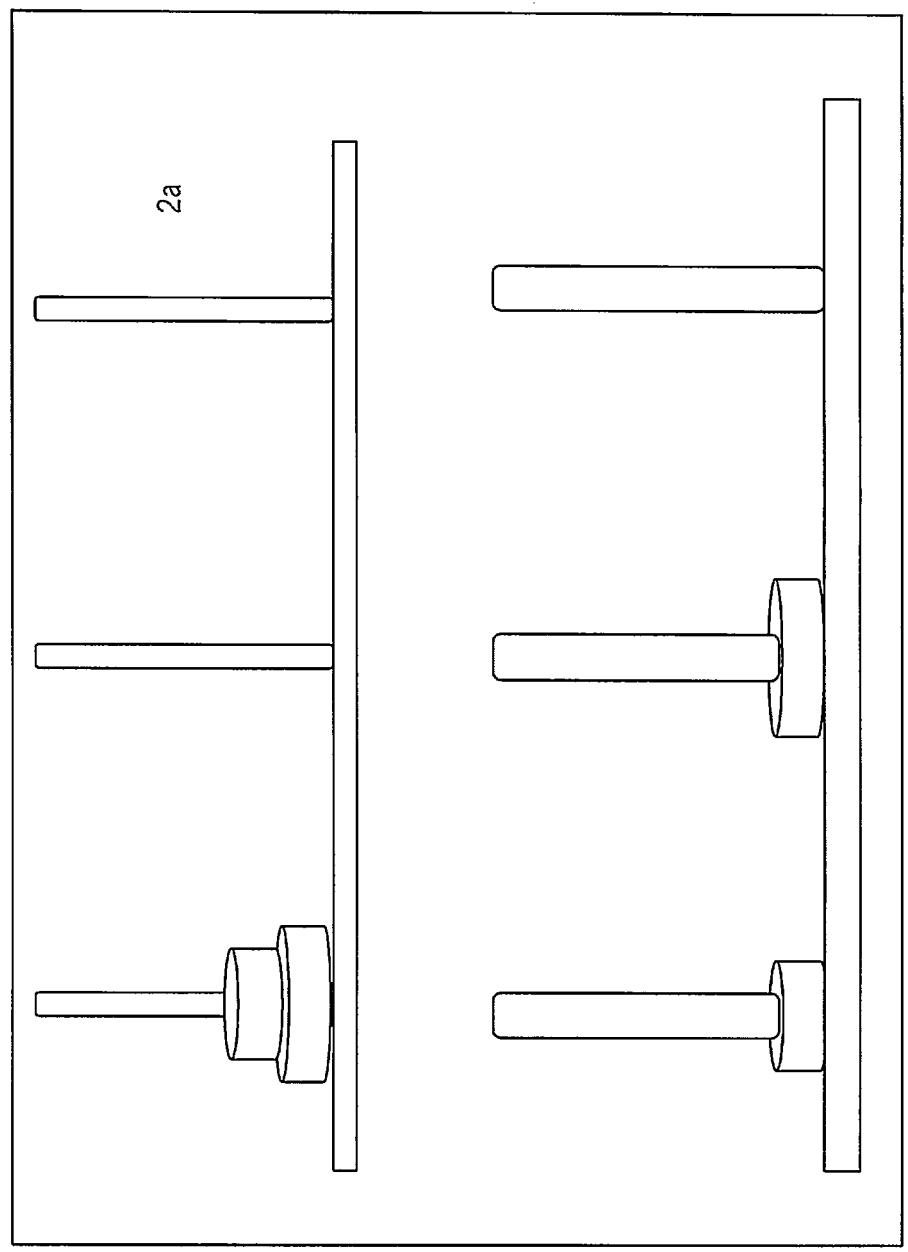
FIG. 13 illustrates an example user interface for administering and scoring multiple level executive functioning tests and tasks.

Turning now to FIG. 13, the Tower subtest may evaluate executive function domains including Cognitive/Behavioral Control, Planning, Cognitive Flexibility (multiple simultaneous tasks), and Rule Violations. As seen in FIG. 13, the examinee GUI for the tower task may display data similar to that in the non-limiting example GUI in FIG. 13, and an examiner GUI may include a client view display, and general and correct/incorrect response instructions, as described above. As seen in FIG. 13, the tower examinee GUI may include a combination of graphics representing pegs, and multiple rings (chips) to be stacked in order on the pegs. The user may select each chip (e.g., by clicking and holding a mouse, for example) to simulate lifting it off of the peg, and thereafter drop the chip onto the same or a different peg. The instructions may direct the examinee to move the chips on the bottom so that they end up in the same order on the same peg as the chips on top, using as few moves as possible.

The examinee may progress through the tower practice test, where correct answers are reinforced and incorrect answers are identified as disclosed above. For example, if the examinee tries to move a chip incorrectly (e.g., tries to touch the floating chip; touches the lower part of the peg; tries to move multiple chips; tries to move the chips on top; etc.), the error feedback may instruct the examinee that the examinee that these moves are incorrect. In this example, the examinee may try again starting with the chips in the previous or original position. In another example, if the instructions limit the examinee to a certain number of moves, and the examinee uses more than the allotted moves, the error feedback may instruct the examinee to complete the tower in the allotted amount of moves or less. In this example, the examinee should try again, possibly with a reset task. In another example, if the instructions designate that a smaller chip should go on a larger one, or vice versa, and the examinee placed the incorrect chip on top of another, the error feedback may instruct the examinee to not place incorrect sized chips on top of others. In this example, the examinee should try again, possibly with a reset task. The examinee may repeat the practice test, and/or take additional practice tests, and after one or more practice tests, the examinee may take the actual test and be scored as described above, according to their ability to correctly move chips to build the tower.

Turning now to FIG. 14, the Social Sorting subtest may include, as non-limiting examples, Category Sorting, and Emotion Sorting tasks, each of which is described in detail below. The Social Sorting subtest may evaluate executive function domains including Cognitive/Behavioral Control, Cognitive Flexibility (multiple simultaneous tasks), Self-Monitoring, and Emotion Regulation.

As seen in FIG. 14, the examinee GUI for the category sorting task may display data similar to that in the non-limiting example GUI in FIG. 14, and an examiner GUI may include a client view display, and general and correct/incorrect response instructions, similar to those seen in FIG. 14, and as described above. As seen in FIG. 14, the category sorting examinee GUI may include 4 key cards at the top of the GUI screen, laid out from left to right in order. The category sorting examinee GUI may further include a "deck" of displayed cards at the bottom of the screen. The instructions may direct the examinee to take the top card on the deck and place it below the key card that the examinee thinks it matches (e.g., move the top card from the deck, and drag it below the key card the examinee thinks it matches, then unclick the mouse, for example). In some embodiments, the instructions may not direct the examinee on how to match the cards, but may notify the examinee each time if the match is right or wrong. As non-limiting examples, the category matching examinee GUI may be testing similarities in person, clothes, etc.

The examinee may progress through the category sorting practice test, where correct answers are reinforced (e.g., the card flashes green) and incorrect answers (e.g., the card flashes red) are identified as disclosed above. For example, if the examinee places the card under the row for an incorrect match, (e.g., person, clothes, or other categories don't match), the error feedback may instruct the examinee that the examinee has incorrectly matched the card showing on the deck, and that the card placed by the examinee does not match the key card in any of the correct ways (e.g., no matching categories). In this example, the instructions may direct the examinee to leave the card and try to get the next one correct, or may create an entirely new group of cards and deck. In this example, the examinee should try again, possibly with a reset group of keycards and deck. The examinee may repeat the practice test, and/or take additional practice tests, and after one or more practice tests, the examinee may take the actual test and be scored as described above, according to their ability to correctly match cards in the deck to the keycards displayed in a row.

Returning now to FIG. 14, the examinee GUI for the emotion sorting task may display data similar to that in the non-limiting example GUI in FIG. 14, and an examiner GUI may include a client view display, and general and correct/incorrect response instructions, similar to those seen in FIG. 14, and as described above. As above, the emotion sorting examinee GUI may include 4 key cards in a row and a deck of displayed cards, and the instructions may direct the examinee to take the top card on the deck and place it below the key card that the examinee thinks it matches. As above, the instructions may not direct the examinee on how to match the cards, but may notify the examinee each time if the match is right or wrong. As non-limiting examples, the emotion matching examinee GUI may be testing similarities in emotions, facial expressions, etc.

The examinee may progress through the emotion sorting practice test, where correct answers are reinforced (e.g., the card flashes green) and incorrect answers (e.g., the card flashes red) are identified as disclosed above. For example, if the examinee places the card under the row for an incorrect match, (e.g., emotion, facial expression, or other emotional cues don't match), the error feedback may instruct the examinee that the examinee has incorrectly matched the card showing on the deck, and that the card placed by the examinee does not match the key card in any of the correct ways (e.g., no matching emotions). In this example, the instructions may direct the examinee to leave the card and try to get the next one correct, or the examinee should try again, possibly with a reset group of keycards and deck. The examinee may repeat the practice test, and/or take additional practice tests, and after one or more practice tests, the examinee may take the actual test and be scored as described above, according to their ability to correctly match cards in the deck to the keycards displayed in a row.

Thus, the Social Sorting subtest may evaluate executive function domains including Cognitive/Behavioral Control; Self-Monitoring; and Emotion Regulation to determine the cognitive abilities of the examinee. Specifically, the category sorting and emotion sorting tasks track the examinee's cognitive abilities to select the correct match between the top card on the deck and one of the cards in the row, according to category and emotion respectively.

The Social Sorting subtest also demonstrates the Cognitive Flexibility executive function domain. The input task data demonstrates multiple simultaneous function skills to determine the cognitive abilities of the examinee being used simultaneously. Specifically, the category and emotion sorting tasks test the examinee's cognitive ability to recognize various means of sorting the cards and matching them accordingly.

Figure 15:
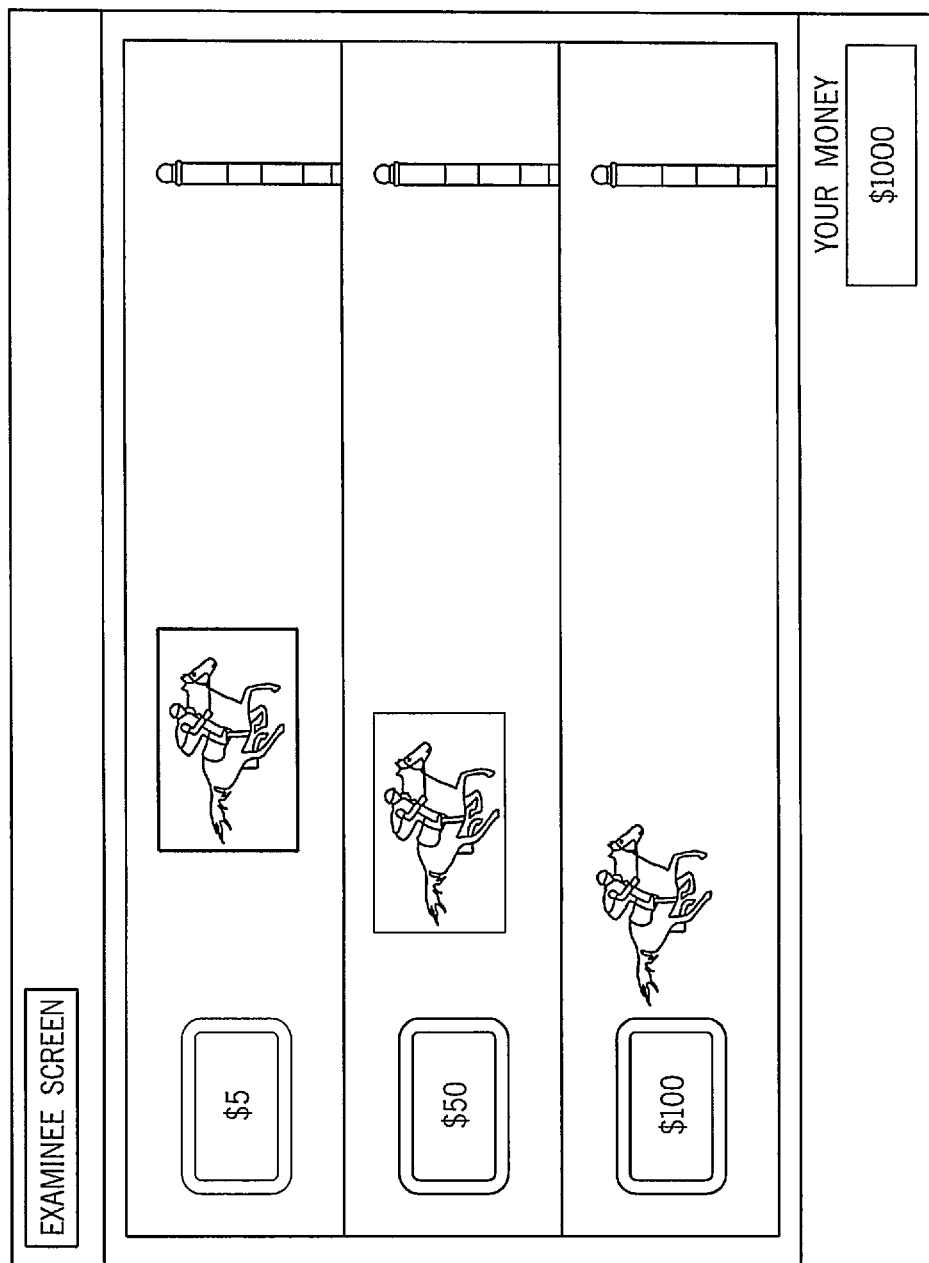
FIG. 15 illustrates an example user interface for administering and scoring multiple level executive functioning tests and tasks.

Turning now to FIG. 15, the Derby subtest may evaluate executive function domains including Cognitive/Behavioral Control; Risk-Taking Control; and Emotion Regulation tests. As seen in FIG. 15, the examinee GUI for the derby task may display data similar to that in the non-limiting example GUI in FIG. 15, and an examiner GUI may include a client view display, and general and correct/incorrect response instructions, as described above. As seen in FIG. 15, the derby examinee GUI may include a combination of graphics representing money denominations, horses and jockeys, racing tracks, a finish line, and a total amount of the examinee's money from the derby task. The instructions may direct the examinee to pretend that they have one thousand dollars to bet on horse races (or in some embodiments, frog races), and to try to win as much money as possible. In this task, the horse closest to the finish line always pays less money if it wins, because it has a shorter distance to run. The horse farthest from the finish line always pays the most, because it has longer to run. But, for each race, any of the horses could win. The instructions may instruct the examinee to play as if it's really their money.

For each race, the examinee may be instructed that to pick a horse by selecting the five, fifty, or one-hundred dollar bet. If the examinee's horse wins, the examinee wins the bet. If the examinee's horse finishes last, the examinee loses the bet. If the examinee's horse finishes second, the examinee doesn't win or lose any money. The instructions may direct the examinee to place their bet quickly, as each race begins after a set time period (e.g., 10 seconds). After each race, the examinee GUI displayed how much money the examinee has.

The examinee may progress through the derby practice test, where correct answers are reinforced and incorrect answers are identified as disclosed above. For example, if the examinee doesn't place a bet in time for the race, the error feedback may instruct the examinee that they failed to place a bet in time for the race. In this example, the examinee may try again the first time without consequence, but in future races may lose money each time this happens. The examinee may repeat the practice test, and/or take additional practice tests, and after one or more practice tests, the examinee may take the actual test and be scored as described above, according to their ability to correctly predict the winning horse and collect the money from the bet.

Figure 16:
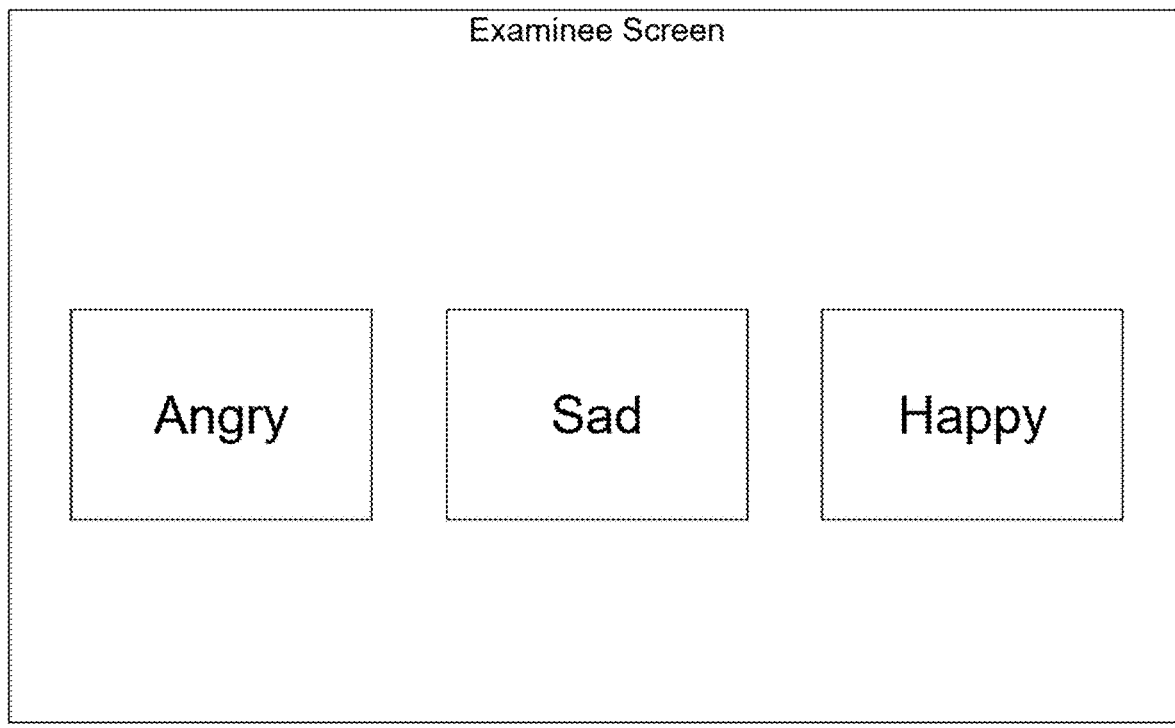
FIG. 16 illustrates an example user interface for administering and scoring multiple level executive functioning tests and tasks.

Turning now to FIG. 16, the Prosody Word Interference subtest may include, as non-limiting examples, Prosody/Word Identification, Prosody/Emotion Naming, Inhibition, and Switching tasks, each of which is described in detail below. The Social Sorting subtest may evaluate executive function domains including Cognitive/Behavioral Control, Cognitive Flexibility, (multiple simultaneous tasks), Inhibitory Control, and Emotion Regulation.

Returning now to FIG. 16, the examinee GUI for the prosody/word identification task may display data similar to that in the non-limiting example GUI in FIG. 16, and an examiner GUI may include a client view display, and general and correct/incorrect response instructions, as described above. As seen in FIG. 16, the prosody/word identification examinee GUI may include a series of boxes, each of which includes a character string forming a word describing an emotion (e.g., angry, sad, happy, etc.). The user interface may also include an audio file with a voice stating one of the emotions (e.g., "angry," "sad," "happy," etc.). The instructions may direct the examinee to select the box that matches the word in the audio file, so if the examinee hears the word angry, sad, or happy, the examinee selects the matching box containing the word angry, sad, or happy. In some embodiments, the instructions may direct the examinee to listen carefully, as the audio sample will only be played once.

The examinee may progress through the prosody/word identification practice test, where correct answers are reinforced and incorrect answers are identified, possibly using visual feedback, and/or as disclosed above. For example, if the word is happy, and the examinee selects the box containing the word angry, the error feedback may instruct the examinee that the examinee should select the word that matches the word in the audio sample. In this example, the examinee may try again starting at the last audio sample, or may be provided with a new audio sample. The examinee may repeat the practice test, and/or take additional practice tests, and after one or more practice tests, the examinee may take the actual test and be scored as described above, according to their selection of the correct box containing the word stated in the audio sample.

Returning now to FIG. 16, the examinee GUI for the prosody/emotion naming task may display data similar to that in the non-limiting example GUI in FIG. 16, and an examiner GUI may include a client view display, and general and correct/incorrect response instructions, as described above. As seen in FIG. 16, the prosody naming examinee GUI may include a series of boxes as described above. The user interface may also include an audio file with a voice making a statement (e.g., "goodbye") in a certain tone of voice. The instructions may direct the examinee to select the box that matches the tone of voice, so if the examinee hears a happy voice, the examinee would select the box containing the word happy. In some embodiments, the instructions may direct the examinee to listen carefully, as the audio sample will only be played once.

The examinee may progress through the prosody/emotion naming practice test, where correct answers are reinforced and incorrect answers are identified, possibly using visual feedback, and/or as disclosed above. For example, if the tone of voice is angry and the examinee selects the box containing the word happy, the error feedback may instruct the examinee that the examinee should select the word that matches the tone of voice (e.g., angry). In this example, the examinee may try again starting at the last audio sample, or may be provided with a new audio sample. The examinee may repeat the practice test, and/or take additional practice tests, and after one or more practice tests, the examinee may take the actual test and be scored as described above, according to their selection of the correct tone of voice in the audio sample.

Returning now to FIG. 16, the examinee GUI for the prosody naming inhibition task may display data similar to that in the non-limiting example GUI in FIG. 16, and an examiner GUI may include a client view display, and general and correct/incorrect response instructions, as described above. As seen in FIG. 16, the prosody naming examinee GUI may include a series of boxes as described above. The user interface may also include an audio file with a voice stating a word (e.g., angry, sad, or happy). However, for the inhibition task, the tone of voice for the word may reflect a different emotion than the word itself (e.g., the word angry, said in a sad tone of voice). The instructions may direct the examinee to select the box that matches the tone of voice, not the word they hear, so in the example above, if the examinee hears a sad voice saying the word angry, the examinee would select the box containing the word sad. The converse may also be tested, where the examinee selects the word spoken, and not the tone of voice. In some embodiments, the instructions may direct the examinee to listen carefully, as the audio sample will only be played once.

The examinee may progress through the inhibition practice test, where correct answers are reinforced and incorrect answers are identified, possibly using visual feedback, and/or as disclosed above. For example, if the tone of voice is sad and the examinee selects the box containing the word angry, the error feedback may instruct the examinee that the examinee should select the word that matches the voice (e.g., sad), and not the word spoken in the audio sample (e.g., angry). The converse may also be true. In this example, the examinee may try again starting at the last audio sample, or may be provided with a new audio sample. The examinee may repeat the practice test, and/or take additional practice tests, and after one or more practice tests, the examinee may take the actual test and be scored as described above, according to their selection of the correct tone of voice, and not the spoken word, or vice versa, according to the instructions.

The GUI and other parameters for the practice test and actual test for the prosody switching task may have any or all characteristics described above for the prosody/word identification, the prosody/emotion naming, and/or the prosody inhibition tasks described above. However, in addition to directing the examinee to select the correct box containing the word or emotion in the series of boxes, the instructions may further direct the examinee that if a box in the series of boxes includes a visual indicator (e.g., the outline or background for the box is yellow), to select either a box that matches the word in the audio sample, or to select the box that matches the emotion reflected in the audio sample, thereby switching between identifying words and identifying emotions according to the instructions.

The examinee may progress through the word/emotion switching practice test, where correct answers are reinforced and incorrect answers are identified as disclosed above. For example, in addition to the error feedback provided in the prosody/word identification, prosody/emotion naming, and word/emotion task inhibition examples above, if the examinee selects a word matching the word in the audio sample, because of the yellow outline around or background within the box, when they should have selected the word describing the emotion in the audio sample, or vice versa, according to the instructions, the error feedback may instruct the examinee that the examinee should switch when the yellow outline is around, or background is within, the box, according to the instructions. In this example, the examinee should try again starting at the last correct word or emotion match selection, or possibly creating a new examinee GUI. The examinee may repeat the practice test, and/or take additional practice tests, and after one or more practice tests, the examinee may take the actual test and be scored as described above, according to their selection of correct matches to words and emotions, based on the visual indicator and the instructions.

Thus, the Prosody Word Interference subtest may evaluate executive function domains including Cognitive/Behavioral Control, Inhibitory Control, and Emotion Regulation to determine the cognitive abilities of the examinee. Specifically, the word identification, emotion naming, and inhibition tasks track the examinee's cognitive abilities to select the correct word matching the word or emotion of the audio sample.

The Prosody Word Interference subtest also demonstrates the Cognitive Flexibility executive function domain. The input task data demonstrates multiple simultaneous function skills to determine the cognitive abilities of the examinee being used simultaneously. Specifically, the inhibition task tests the examinee's cognitive ability to select the emotion in the voice of the audio sample, rather than the word itself (or vice versa). The switching task tracks the examinee's cognitive ability to switch while maintaining the ability to select the correct emotion or word according to the visual indicator (e.g., yellow outline or background) and instructions.

Figure 17:
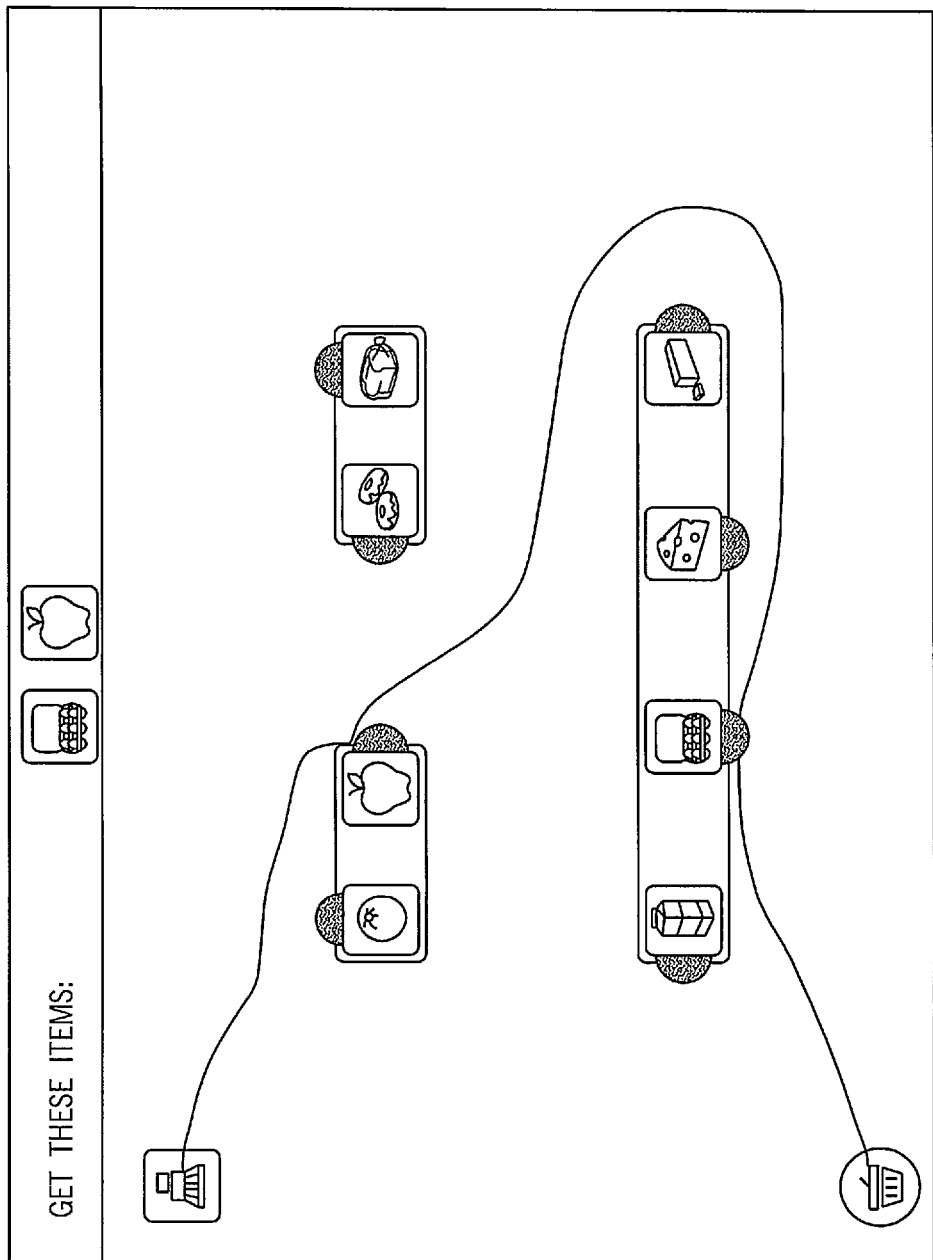
FIG. 17 illustrates an example user interface for administering and scoring multiple level executive functioning tests and tasks.

Turning now to FIG. 17, the Grocery List subtest evaluates executive function domains including Cognitive/Behavioral Control, Planning, Inhibitory Control, and Rule Violations. As seen in FIG. 17, the examinee GUI for the grocery list task may display data similar to that in the non-limiting example GUI in FIG. 17, and an examiner GUI may include a client view display, and general and correct/incorrect response instructions, as described above. As seen in FIG. 17, the grocery list examinee GUI may include a series of graphical representations of: a grocery cart, a checkout register, and a series of shelves, aisles, and various grocery products, as well as a shopping list displayed at the top of the screen representing the grocery products to be collected. The instructions may direct the examinee that the GUI displays a virtual grocery store with shelves and aisles, and that the user should draw a line to select the grocery items displayed at the top of the screen using the shortest path from the basket to the checkout register graphic without reentering any of the displayed aisles.

The instructions may further instruct the examinee regarding rules: that the examinee must start with the grocery cart; that the examinee must move in a single continuous line (which the shopping cart graphic may follow as created); that if the examinee stops and changes position of the input that the examinee must return to the previously drawn line to continue; that the examinee must not draw a path through a shelf; etc. In some embodiments, the examinee must select at least one of a type of grocery item (e.g., fruit).

The examinee may progress through the grocery list practice test, where correct answers are reinforced and incorrect answers are identified as disclosed above. For example, if the examinee reenters an aisle, the error feedback may instruct the examinee that the examinee should only enter each aisle once. If the examinee doesn't take the shortest path, the error feedback may instruct the examinee to take the shortest path, and possibly demonstrate such a path. If the examinee doesn't include the at least one type of grocery item, the error feedback may instruct the examinee to select such an item. In these examples, the examinee may try again starting at the beginning or from their last correct position. The examinee may repeat the practice test, and/or take additional practice tests, and after one or more practice tests, the examinee may take the actual test and be scored as described above, according to their selection of the grocery items according to the instructions.

Other embodiments and uses of the above inventions will be apparent to those having ordinary skill in the art upon consideration of the specification and practice of the invention disclosed herein. The specification and examples given should be considered exemplary only, and it is contemplated that the appended claims will cover any other such embodiments or modifications as fall within the true scope of the invention.

The Abstract accompanying this specification is provided to enable the United States Patent and Trademark Office and the public generally to determine quickly from a cursory inspection the nature and gist of the technical disclosure and in no way intended for defining, determining, or limiting the present invention or any of its embodiments.

The invention claimed is:

1. A system comprising a server hardware computing device coupled to a network and comprising at least one processor executing specific computer-executable instructions within a memory that, when executed, cause the system to:
generate:
a first series of user interface objects selected from a database coupled to a network, and comprising:
a first sequence including a plurality of letters; or
a plurality of character string descriptions, each character string in the plurality of character strings comprising a color character string or a user interface characteristic character string;
a second series of user interface objects selected from the database and comprising:
a second sequence including a plurality of numbers; or
a plurality of user interface characteristics including a color or a characteristic of a user interface object in the first series of user interface objects or the second series of user interface objects;
a third series of user interface objects comprising a plurality of visual or audio distractors designed to pull the attention of a user from the first series of user interface objects or the second series of user interface objects;
at least one visual indicator display object selected from the database and requiring, according to a logic or at least one rule within the specific computer-executable instructions, a switch, alternating between the first series of user interface objects, and the second series of user interface objects;
encode, for display on a client hardware computing device comprising an examinee client device or an examiner client device, a graphical user interface (GUI) comprising the first series of user interface objects, the second series of user interface objects, the third series of user interface objects, and the at least one visual indicator display object;
decode, from the GUI, an electronic input from the user switching from the first series of user interface objects, displayed in association with the visual indicator display object, to the second series of user interface objects;
responsive to the electronic input failing to match a correct response associated in the database with a task data defining a function skill demonstrating a cognitive ability of a user, calculate a score;
pause additional input into the GUI;
update a content within the GUI to include:
an identification of the electronic input as incorrect;
a visual cue for the electronic input failing to match the correct response;
and
a last correct input from which to continue; transmit a real-time rendering of the GUI and the electronic input to the examiner client device for display on an examiner GUI;
display, on the examiner GUI an instruction for how to proceed; and
compare the score with a previous score for a task not including the third series of user interface objects.

2. The system of claim 1, wherein-the GUI displayed on the examiner client device includes:
an electronic output providing the user with instructions for providing the electronic input;
a first GUI control for monitoring the electronic input received from the user; or
a second GUI control for demonstrating a correct response and an incorrect response by the user.

3. The system of claim 1, wherein the electronic input comprises a selection by the user, via a touch screen, a stylus, or an electronic mouse, of each element within the first sequence or the second sequence, and wherein the GUI does not display an order of the selection of each element.

4. The system of claim 3, wherein a second task associated with the second series of user interface objects requires a greater interactivity by the user than a first task associated with the first series of user interface objects, and a third task requires a greater interactivity by the user than the second task.

5. The system of claim 3, wherein:
the first series of user interface objects includes the plurality of letters;
the second series of user interface objects includes the plurality of numbers;
the third series of user interface objects includes a plurality of letters or numbers visually distinct from the first series of user interface objects or the second series of user interface objects;
a first user input decoded by the server hardware computing device comprises the first user input selecting, alternatively, the plurality of letters and the plurality of numbers;
a second user input decoded by the server hardware computing device comprises the second user input following a selection of a first number including the at least one visual indicator with a second number, or, following a selection of a first letter including the at least one visual indicator with a second letter; and
a third user input decoded by the server hardware computing device comprises the third user input moving sequentially between the first series of user interface objects or the second series of user interface objects without a visual reminder, displayed on the GUI, indicating a previously selected letter or number.

6. The system of claim 5, wherein each of the third series of user interface objects is displayed on the GUI in close proximity to at least one of the first series or the second series of user interface objects displaying an identical letter or numeric value.

7. The system of claim 6, wherein each of the first series and the second series of user interface objects are enclosed within a circle and, each of the third series of user interface objects is not enclosed within a circle.

8. The system of claim 1, wherein:
the GUI displays a plurality of character strings, each character string representing the color, and each character string being displayed in a font color;
a first user input decoded by the server hardware computing device comprises the first user input selecting a character string from the plurality of character strings matching a second character string;
a second user input decoded by the server hardware computing device comprises the second user input selecting a character string from the plurality of character strings wherein the font color matches a color described by the second character string; and
a third user input decoded by the server hardware computing device comprises a visual cue, wherein, if the visual clue is displayed on the GUI the third user input selects the character string matching the second character string, but if the visual clue is not displayed on the GUI, the third user input selects the font color matching the second character string.

9. The system of claim 8, wherein the first series of user interface objects is visually offset from, or contains a different background color from, the second series of user interface objects.

10. A method comprising:
generating, by a server hardware computing device coupled to a network and comprising at least one processor executing specific computer-executable instructions within a memory:
a first series of user interface objects selected from a database coupled to a network, and comprising:

a first sequence including a plurality of letters; or a plurality of character string descriptions, each character string in the plurality of character strings comprising a color character string or a user interface characteristic character string;

a second series of user interface objects selected from the database and comprising:

a second sequence including a plurality of numbers; or a plurality of user interface characteristics including a color or a characteristic of a user interface object in the first series of user interface objects or the second series of user interface objects;

a third series of user interface objects comprising a plurality of visual or audio distractors designed to pull the attention of a user from the first series of user interface objects or the second series of user interface objects;

at least one visual indicator display object selected from the database and requiring, according to a logic or at least one rule within the specific computer-executable instructions, a switch, alternating between the first series of user interface objects, and the second series of user interface objects;

encoding, by the server hardware computing device, for display on a client hardware computing device comprising an examinee client device or an examiner client device, a graphical user interface (GUI) comprising the first series of user interface objects, the second series of user interface objects, the third series of user interface objects, and the at least one visual indicator display object;

decoding, by the server hardware computing device, from the GUI, an electronic input from the user switching from the first series of user interface objects, displayed in association with the visual indicator display object, to the second series of user interface objects;

responsive to the electronic input failing to match a correct response associated in the database with a task data defining a function skill demonstrating a cognitive ability of a user, calculate a score:

pausing additional input into the GUI;

updating a content within the GUI to include:

an identification of the electronic input as incorrect;

a visual cue for the electronic input failing to match the correct response; and a last correct input from which to continue;

transmitting a real-time rendering of the GUI and the electronic input to the examiner client device for display on an examiner GUI; and displaying, on the examiner GUI an instruction for how to proceed; and comparing, by the server hardware computing device, the score with a previous score for a task not including the third series of user interface objects.

11. The method of claim 10, wherein-the GUI displayed on the examiner client device includes:

an electronic output providing the user with instructions for providing the electronic input;

a first GUI control for monitoring the electronic input received from the user; or a second GUI control for demonstrating a correct response and an incorrect response by the user.

12. The method of claim 10, wherein the electronic input comprises a selection by the user, via a touch screen, a stylus, or an electronic mouse, of each element within the first sequence or the second sequence, and wherein the GUI does not display an order of the selection of each element.

13. The method of claim 12, wherein a second task associated with the second series of user interface objects requires a greater interactivity by the user than a first task associated with the first series of user interface objects, and a third task requires a greater interactivity by the user than the second task.

14. The method of claim 12, wherein:

the first series of user interface objects includes the plurality of letters;

the second series of user interface objects includes the plurality of numbers;

the third series of user interface objects includes a plurality of letters or numbers visually distinct from the first series of user interface objects or the second series of user interface objects;

a first user input decoded by the server hardware computing device comprises the first user input selecting, alternatively, the plurality of letters and the plurality of numbers;

a second user input decoded by the server hardware computing device comprises the second user input following a selection of a first number including the at least one visual indicator with a second number, or, following a selection of a first letter including the at least one visual indicator with a second letter; and a third user input decoded by the server hardware computing device comprises the third user input moving sequentially between the first series of user interface objects or the second series of user interface objects without a visual reminder, displayed on the GUI, indicating a previously selected letter or number.

15. The method of claim 14, wherein each of the third series of user interface objects is displayed on the GUI in close proximity to at least one of the first series or the second series of user interface objects displaying an identical letter or numeric value.

16. The method of claim 15, wherein each of the first series and the second series of user interface objects are enclosed within a circle and, each of the third series of user interface objects is not enclosed within a circle.

17. The method of claim 10, wherein:

the GUI displays a plurality of character strings, each character string representing the color, and each character string being displayed in a font color;

a first user input decoded by the server hardware computing device comprises the first user input selecting a character string from the plurality of character strings matching a second character string;

a second user input decoded by the server hardware computing device comprises the second user input selecting a character string from the plurality of character strings wherein the font color matches a color described by the second character string; and a third user input decoded by the server hardware computing device comprises a visual cue, wherein, if the visual clue is displayed on the GUI the third user input selects the character string matching the second character string, but if the visual clue is not displayed on the GUI, the third user input selects the font color matching the second character string.

18. The method of claim 17, wherein the first series of user interface objects is visually offset from, or contains a different background color from, the second series of user interface objects.

* * * * *